United States Patent
Kwon et al.

(10) Patent No.: US 9,770,300 B2
(45) Date of Patent: *Sep. 26, 2017

(54) SURGICAL ROBOT AND CONTROL METHOD THEREOF

(71) Applicant: Samsung Electronics Co., Ltd., Suwon-Si, Gyeonggi-Do (KR)

(72) Inventors: Young Do Kwon, Yongin-si (KR); Kee Hong Seo, Seoul (KR); Kyung Shik Roh, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 198 days.

This patent is subject to a terminal disclaimer.

(21) Appl. No.: 14/333,039

(22) Filed: Jul. 16, 2014

(65) Prior Publication Data

US 2015/0066051 A1 Mar. 5, 2015

(30) Foreign Application Priority Data

Sep. 4, 2013 (KR) .................. 10-2013-0106276

(51) Int. Cl.
*G06F 19/00* (2011.01)
*A61B 19/00* (2006.01)
(Continued)

(52) U.S. Cl.
CPC .......... *A61B 19/2203* (2013.01); *A61B 34/30* (2016.02); *A61B 34/37* (2016.02);
(Continued)

(58) Field of Classification Search
CPC .... A61B 19/2203; B25J 13/025; B25J 9/1633
(Continued)

(56) References Cited

U.S. PATENT DOCUMENTS 5,807,377 A * 9/1998 Madhani ................ A61B 34/77
606/1
6,468,265 B1 * 10/2002 Evans .................... A61B 34/32
600/103
(Continued)

FOREIGN PATENT DOCUMENTS

KR 100997194 B1 11/2010
WO WO-98/51451 A2 11/1998
(Continued)

OTHER PUBLICATIONS

European Search Report dated Jan. 29, 2015 issued in corresponding European Application No. 14183492.9.
(Continued)

*Primary Examiner* — Harry Oh
(74) *Attorney, Agent, or Firm* — Harness, Dickey & Pierce, P.L.C.

(57) ABSTRACT

A master console includes handles configured to control robotic surgical instruments of a slave robot, force/torque detectors configured to detect forces applied to the handles by an operator, a force compensator configured to generate force control signals that cancel out the forces applied to the handles by the operator, and a master controller configured to drive at least one joint of each of the handles in order to control motion of the handles based on motion control signals and the generated force control signals.

14 Claims, 12 Drawing Sheets

(51) Int. Cl.
*B25J 9/16* (2006.01)
*B25J 13/02* (2006.01)
*B25J 3/04* (2006.01)
*A61B 34/30* (2016.01)
*A61B 34/37* (2016.01)
*A61B 34/00* (2016.01)
*A61B 90/00* (2016.01)

(52) U.S. Cl.
CPC .............. *A61B 34/74* (2016.02); *A61B 34/76* (2016.02); *A61B 34/77* (2016.02); *B25J 3/04* (2013.01); *B25J 9/1633* (2013.01); *B25J 13/025* (2013.01); *A61B 2090/064* (2016.02)

(58) Field of Classification Search
USPC ......................................................... 700/245
See application file for complete search history.

(56) References Cited

U.S. PATENT DOCUMENTS

| | | | | |
|---|---|---|---|---|
| 6,594,552 | B1* | 7/2003 | Nowlin .................. | B25J 9/1689 318/568.11 |
| 6,699,177 | B1* | 3/2004 | Wang ..................... | A61B 34/75 414/2 |
| 7,752,920 | B2 | 7/2010 | Blumenkranz et al. | |
| 2003/0195661 | A1* | 10/2003 | Wang ..................... | A61B 34/77 700/258 |
| 2007/0013336 | A1* | 1/2007 | Nowlin .............. | A61B 19/2203 318/568.21 |
| 2007/0151391 | A1* | 7/2007 | Larkin ................... | A61B 34/70 74/490.06 |
| 2008/0046122 | A1* | 2/2008 | Manzo ............... | A61B 1/00149 700/245 |
| 2010/0094312 | A1* | 4/2010 | Ruiz Morales ........ | B25J 13/085 606/130 |
| 2011/0020779 | A1* | 1/2011 | Hannaford ............ | G06F 19/327 434/262 |
| 2011/0071543 | A1* | 3/2011 | Prisco ................ | A61B 17/0218 606/130 |
| 2012/0078053 | A1* | 3/2012 | Phee .................. | A61B 1/00147 600/139 |
| 2013/0011220 | A1* | 1/2013 | Jacobsen .................... | B25J 3/04 414/2 |
| 2014/0142592 | A1* | 5/2014 | Moon ................ | A61B 19/2203 606/130 |

FOREIGN PATENT DOCUMENTS

WO   WO-2008049898 A1   5/2008
WO   WO-2012/149435 A2   11/2012

OTHER PUBLICATIONS

European Search Report dated Sep. 27, 2016 issued in corresponding European Patent Application No. 14183492.9.

\* cited by examiner

SURGICAL ROBOT AND CONTROL METHOD THEREOF

CROSS-REFERENCE TO RELATED APPLICATION

This application claims the benefit of Korean Patent Application No. 10-2013-0106276, filed on Sep. 4, 2013 in the Korean Intellectual Property Office, the entire disclosure of which is incorporated herein by reference.

BACKGROUND

1. Field

Example embodiments relate to a surgical robot and a control method thereof. Example embodiments also relate to a surgical robot and a control method thereof which may feed force, applied to a robotic surgical instrument from an external environment (human body tissues), back to a master console without provision of a sensor to measure such force in a slave robot, if the robotic surgical instrument provided on a robot arm of the slave robot contacts the external environment.

2. Description of the Related Art

Minimally invasive surgery is known as surgery minimizing or reducing the size of a diseased part. Differently from open surgery conducted through a relatively large surgical window formed through a portion (for example, the abdomen) of a human body, minimally invasive surgery is conducted by observing an image after a video camera and various surgical instruments are inserted into the abdomen of a human body through at least one surgical hole (or invasive hole) having a size of 0.5~1.5 cm formed in the abdomen.

Such minimally invasive surgery causes relatively little pain after surgery, allows a patient to rapidly recover intestinal function and resume consumption of solid food rapidly, reduces hospital stay, allows the patient to rapidly return to a normal state, and has improved aesthetics due to a relatively narrow incisive range, differently from open surgery. Due to these advantages, minimally invasive surgery has been used in cholecystectomy, prostate cancer surgery and herniorrhaphy, and application thereof has begun to increase.

A surgical robot used in minimally invasive surgery includes a master console and a slave robot. The master console generates a control signal according to operation of a surgeon and transmits the generated control signal to the slave robot. The slave robot is operated according to the control signal received from the master console.

The slave robot is provided with at least one robot arm, and a robotic surgical instrument is mounted at the end of each robot arm. Here, the robotic surgical instrument is inserted into the body of a patient through an incision point of the patient. On the other hand, the robot arm is located at the outside of the incision point, and serves to maintain the position and pose of the robotic surgical instrument during surgery.

If the robotic surgical instrument contacts an external environment (for example, human body tissues) during surgery, it may be necessary to feed force, received by the robotic surgical instrument from the external environment, back to the master console.

SUMMARY

Example embodiments provide a surgical robot and a control method thereof which may feed force, received by a robotic surgical instrument from an external environment (human body tissues), back to a master console without provision of a sensor to measure such force in a slave robot, if the robotic surgical instrument provided on a robot arm of the slave robot contacts the external environment.

Additional aspects of the example embodiments will be set forth in part in the description which follows and, in part, will be obvious from the description, or may be learned by practice of the inventive concepts.

In accordance with example embodiments, a master console of a surgical robot includes handles configured to control robotic surgical instruments of a slave robot, force/torque detectors configured to detect forces applied to the handles by an operator, a force compensator configured to generate force control signals that cancel out the forces applied to the handles by the operator, and a master controller configured to drive at least one joint of each of the handles in order to control motion of the handles based on motion control signals and the generated force control signals.

In accordance with example embodiments, a surgical robot includes a slave robot including robotic surgical instruments, and a master console configured to detect forces applied to handles by an operator in order to control the robotic surgical instruments of the slave robot, and configured to drive at least one joint of each of the handles in order to control motion of the handles based on motion control signals and force control signals that cancel out the detected forces, wherein the slave robot is configured to drive at least one joint of each of the robotic surgical instruments in order to control motion of the robotic surgical instruments to follow motion of the handles based on the force control signals and the motion control signals.

In accordance with example embodiments, a slave robot is configured to perform a surgical procedure based on instructions received from a master console, and the slave robot includes a plurality of robotic surgical instruments configured to be inserted into a cavity, the plurality of robotic surgical instruments including at least one joint, a position/velocity error compensator configured to generate motion control signals in order to compensate for differences between a position and a velocity of the at least one joint of each of the robotic surgical instruments and a target position and a target velocity for the at least one joint of each of the robotic surgical instruments received from the master console, and a slave controller configured to drive the at least one joint of each of the robotic surgical instruments to follow motion of handles of the master console based on the generated motion control signals and force control signals received from the master console.

BRIEF DESCRIPTION OF THE DRAWINGS

These and/or other aspects of the inventive concepts will become apparent and more readily appreciated from the following description of the embodiments, taken in conjunction with the accompanying drawings of which.

DETAILED DESCRIPTION

Figure 1:
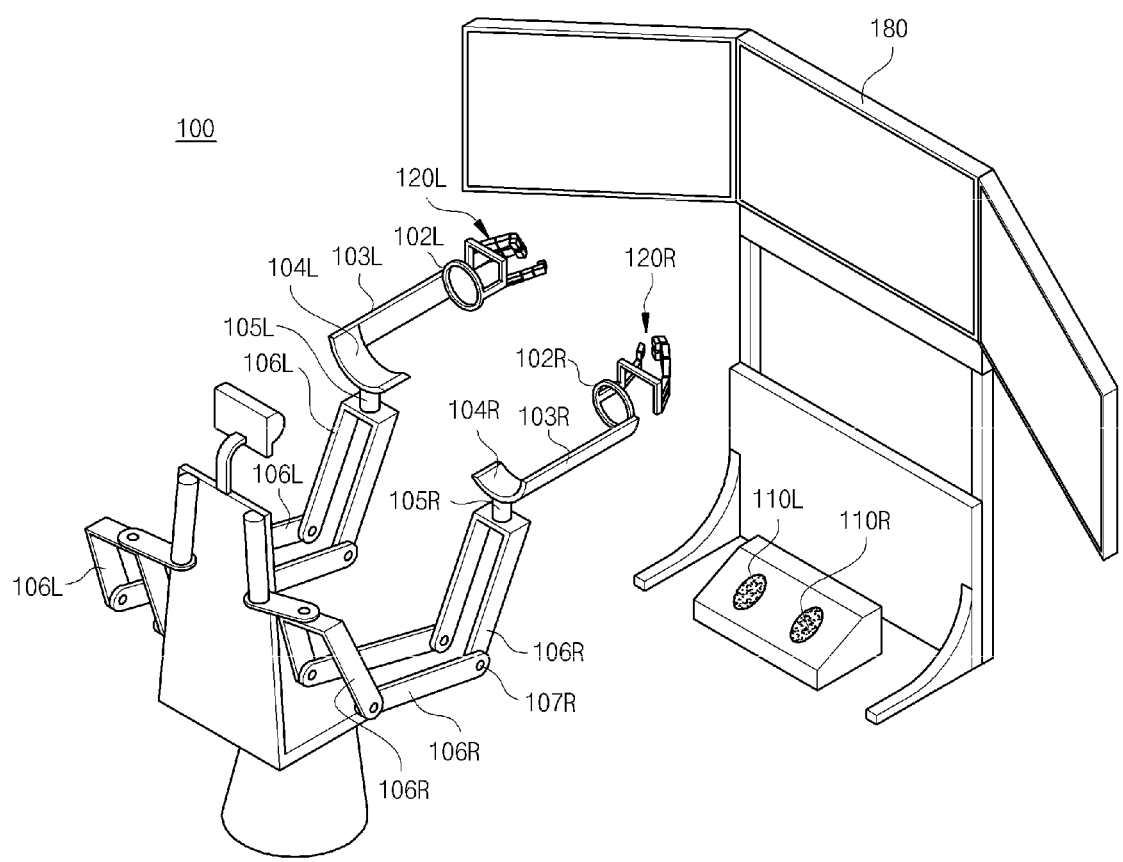
FIG. 1 is a perspective view illustrating the external appearance of a master console of a surgical robot in accordance with example embodiments.

Reference will now be made in detail to embodiments of the inventive concepts, examples of which are illustrated in the accompanying drawings, wherein like reference numerals refer to like elements throughout. Those skilled in the art will appreciate that various modifications, additions, and substitutions to specific elements are possible, without departing from the scope and spirit of the accompanying claims.

Hereinafter, surgical robots and control methods thereof in accordance with example embodiments will be described with reference to the accompanying drawings. In the drawings, the same or similar elements are denoted by the same reference numerals even though they are depicted in different drawings.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments may be applied to a multi-port surgical robot or a single port surgical robot. The multi-port surgical robot refers to a robot configured to insert a plurality of robotic surgical instruments into the abdominal cavity of a patient through individual points. On the other hand, the single port surgical robot refers to a robot configured to insert a plurality of robotic surgical instruments into the abdominal cavity of a patient through one point. In the following description, a single port surgical robot (hereinafter, referred to as a 'surgical robot') will be described.

The surgical robot includes a master console and a slave robot. The master console is a device having a remote control function with respect to the slave robot. The master console transmits a control signal according to the operation of an operator to the slave robot. The slave robot receives the control signal from the master console. The slave robot moves according to the received control signal, and applies operation required for surgery to a patient. Here, the operator may mean medical personnel, e.g., a medical specialist or a doctor. Otherwise, the operator may include a person having qualifications equivalent to medical personnel or an educated person. Broadly, the operator may include a user controlling the operation of the surgical robot.

FIG. 1 is a view illustrating the external appearance of a master console of a surgical robot in accordance with example embodiments.

As shown in FIG. 1, the master console 100 may include an input unit 110L, 110R, 120L, and 120R, and displays 180.

The input unit 110L, 110R, 120L, and 120R receives instructions to remotely operate the slave robot 200 (with reference to FIG. 2) from an operator. For example, the input unit 110L, 110R, 120L, and 120R may include at least one of handles 120L and 120R and clutch pedals 110L and 110R. FIG. 1 illustrates the input unit 110L, 110R, 120L, and 120R as including two clutch pedals 110L and 110R and two handles 120L and 120R.

The clutch pedals 110L and 110R may be used to switch between operation modes of the surgical robot. For example, if the left clutch pedal 110L is operated, a guide tube operation mode may be performed, and if the right clutch pedal 110R is operated, a robotic surgical instrument operation mode may be performed. When the guide tube operation mode is performed, the operator may change the position and pose of a guide tube 210 (with reference to FIG. 2) by operating the handles 120L and 120R. Further, when the robotic surgical instrument operation mode is performed, movement of the guide tube 210 is stopped and the operator may change the positions and poses of robotic surgical instruments by operating the handles 120L and 120R.

According to example embodiments, the robotic surgical instrument operation mode may be divided into an endoscope operation mode and a surgical tool operation mode. For example, the operator may perform the endoscope operation mode or the surgical tool operation mode by applying pressure to the right clutch pedal 110R a predetermined or given number of times or applying pressure to the right clutch pedal 110R for a predetermined or given time.

If the endoscope operation mode is performed, the operator may control the motion of a robotic surgical instrument provided with an endoscope by operating the handles 120L and 120R. While the endoscope operation mode is performed, movement of robotic surgical instruments provided with surgical tools may be stopped. If the surgical tool operation mode is performed, the operator may control the motion of the robotic surgical instruments provided with surgical tools by operating the handles 120L and 120R. While the surgical tool operation mode is performed, movement of the robotic surgical instrument provided with an endoscope may be stopped.

The handles 120L and 120R control movement of a robot arm or robotic surgical instruments provided on the slave robot 200. The handles 120L and 120R may be implemented as haptic devices. The haptic devices may include, for example, at least one multi-joint robot finger. The at least one multi-joint robot finger may be disposed in a shape similar to that of a human hand. FIG. 1 illustrates that three multi-joint robot fingers are provided at positions corresponding to the thumb, the forefinger, and the middle finger of a human hand.

Although FIG. 1 illustrates the handles 120L and 120R as including three multi-joint robot fingers, the number and positions of the multi-joint robot fingers are not limited thereto. For example, the handles 120L and 120R may be provided with multi-joint robot fingers smaller or greater in number than three, and these multi-joint robot fingers may be provided at positions corresponding to the thumb, the index finger, the middle finger, the ring finger, and the little finger of a human hand.

Further, each of the multi-joint robot fingers may include plural links and plural joints. Here, the joint means a connection region between one link and another link. The joint may have at least 1 degree of freedom (DOF). DOF denotes DOF in forward kinematics or inverse kinematics. The DOF of a mechanism refers to the number of independent movements of the mechanism or the number of variables determining independent movements of relative positions of respective links. For example, an object in 3D space formed by the X-axis, the Y-axis, and the Z-axis has at least 1 DOF from among 3 DOF to determine the spatial position of the object (positions of the object on the respective axes) and 3 DOF to determine the spatial orientation of the object (rotation angles of the object about the respective axes). In more detail, it may be understood that, if the object is movable along the respective axes and is rotatable about the respective axes, the object has 6 DOF.

Further, a detection unit to detect information (hereinafter, state information) regarding the state of each joint may be provided at each joint of the multi-joint robot fingers. Here, the detection unit may include a position detection unit to detect the position of each joint (i.e., a joint angle), and a velocity detection unit to detect the velocity of each joint.

The front ends of the multi-joint fingers may be regarded as end effecters of the master console 100. For example, a ring-shaped loop may be provided at each of the front ends of the multi-joint robot fingers. Therefore, the operator may insert his/her fingers into the ring-shaped loops. If the operator moves the fingers under the condition that the fingers are inserted into the ring-shaped loops, the multi-joint robot fingers move so as to correspond to movement of the fingers of the operator, and the detection units provided at the respective joints of the multi-joint robot fingers detect information regarding the states of the respective joints.

The positions and velocities of the respective joints detected through the respective detection units are converted into target positions and target velocities which the respective joints of the robotic surgical instruments will follow. The converted target positions and target velocities are transmitted to a slave robot 200 (with reference to FIG. 2) through a network. Here, the network may be a wired network, a wireless network, or a wired/wireless hybrid network.

Although FIG. 1 illustrates the handles 120L and 120R as being provided with the plural multi-joint robot fingers, the shape of the handles 120L and 120R is not limited thereto. As one example, the handles 120L and 120R may be implemented as haptic devices having a pencil shape or a stick shape so that the operator may surround the handles 120L and 120R by hand. As another example, the handles 120L and 120R may be implemented as haptic devices having a scissors shape so that the operator may insert at least his/her two fingers thereinto. As yet another example, the handles 120L and 120R may be implemented as haptic devices having a glove shape so that the operator may insert his/her all fingers thereinto.

Although FIG. 1 illustrates the left handle 120L and the right handle 120R as being implemented as haptic devices including at least one multi-joint finger, the left handle 120L and the right handle 120R may be implemented as haptic devices having different shapes. For example, the left handle 120L may be implemented as a haptic device having a scissors shape, and the right handle 120R may be implemented as a haptic device including at least one multi-joint robot finger.

Left and right support links 103L and 103R are provided. The support links 103L and 103R are mechanically connected to the handles 120L and 120R. The support links 103L and 103R serve to support the arms of the operator from wrists to elbows. For this purpose, the support links 103L and 103R may include wrist support parts 102L and 102R and elbow support parts 104L and 104R.

The wrist support parts 102L and 102R are arranged at positions corresponding to the wrists of the operator. The wrist support parts 102L and 102R may have various shapes. As one example, as shown in FIG. 1, the wrist support parts 102L and 102R may have a circular shape. In this case, the operator may put the hands into the wrist support parts 102L and 102R and, then, insert the tip of the least one finger of each hand into the ring-shaped loop provided at the front end of the multi-joint robot finger. As another example, the wrist support parts 102L and 102R may have a semicircular shape. In this case, opened regions of the semicircular wrist support parts 102L and 102R may be disposed so as to face the inside of the master console 100, i.e., the operator, and curved regions of the semicircular wrist support parts 102L and 102R may be disposed so as to face the outside of the master console 100. Otherwise, the curved regions of the semicircular wrist support parts 102L and 102R may be disposed so as to face the inside of the master console 100 and the opened regions of the semicircular wrist support parts 102L and 102R may be disposed so as to face the outside of the master console 100. Otherwise, the curved regions of the semicircular wrist support parts 102L and 102R may be disposed so as to face the ground and the opened regions of the semicircular wrist support parts 102L and 102R may be disposed in the opposite direction to the ground. Force/torque (F/T) detection units may be provided at the wrist support parts 102L and 102R. The force/torque detection units detect forces applied to the handles 120L and 120R by the operator.

The elbow support parts 104L and 104R may be arranged at positions corresponding to the elbows of the operator. The elbow support parts 104L and 104R may have a U-shape, as shown in FIG. 1. As one example, opened regions of the elbow support parts 104L and 104R may be disposed in the opposite direction to the ground, and curved regions of the elbow support parts 104L and 104R may be disposed so as to face the ground. As another example, the opened regions of the elbow support parts 104L and 104R may be disposed so as to face the inside or outside of the master console 100. In this case, fixing members (not shown) surrounding the elbows of the operator to fix the elbows to the elbow support parts 104L and 104R may be additionally provided on the elbow support parts 104L and 104R.

At least one connection link 106L or 106R is provided between each of the support links 103L and 103R and a chair. The connection links 106L and 106R serve to mechanically connect the support links 103L and 103R to the chair. Joints 105L and 105R are provided between the connection links 106L and 106R and the support links 103L and 103R. The joints 105L and 105R may have at least 1 DOF. If a plurality of connection links 106L and a plurality of connection links 106R are provided at the left and right parts of the master console 100, joints 107L and 107R are provided between the connection links 106L and between the connection links 106R. These joints 107L and 107R may have at least 1 DOF.

FIG. 1 illustrates the two handles 120L and 120R as being mechanically connected to the chair by the support links 103L and 103R and the connection links 106L and 106R. However, the structure of the master console 100 is not limited thereto. For example, the support links 103L and 103R and the connection links 106L and 106R may be omitted from FIG. 1. If the support links 103L and 103R and the connection links 106L and 106R are omitted, each of the handles 120L and 120R may further include a communication unit (not shown) to transmit and receive data through wired communication or wireless communication with the master console 100.

The displays 180 display at least one of image data and surgical information. The image data displayed through the displays 180 may be an image captured by an endoscope 216a (in FIG. 3) of the slave robot 200, or be acquired through image processing of the captured image. Image processing may include at least one of image enlargement, reduction, movement, rotation, combination, and filtering. Such image processing may be performed by at least one of the slave robot 200 and the master console 100. Surgical information displayed through the displays 180 may include biometric information of a patient. For example, the biometric information may be temperature, pulse, respiration, and blood pressure.

One or more displays 180 may be provided. FIG. 1 illustrates three displays 180 disposed in parallel on the master console 100. As one example, plural displays 180 may display different images. In more detail, a main display located in front of the operator may display an image captured by the endoscope. Sub-displays located at the left and right of the main display may display information regarding the operating state of the slave robot and patient information, respectively. As another example, the plural displays 180 may display the same image. In this case, the same image may be displayed through the respective displays 180, or one image may be displayed through the entirety of the plural displays 180.

The above-described displays 180 may be implemented as liquid crystal displays (LCDs), light emitting diodes (LEDs), organic light emitting diodes (OLEDs), plasma display panels (PDPs), or combinations thereof.

Figure 2:
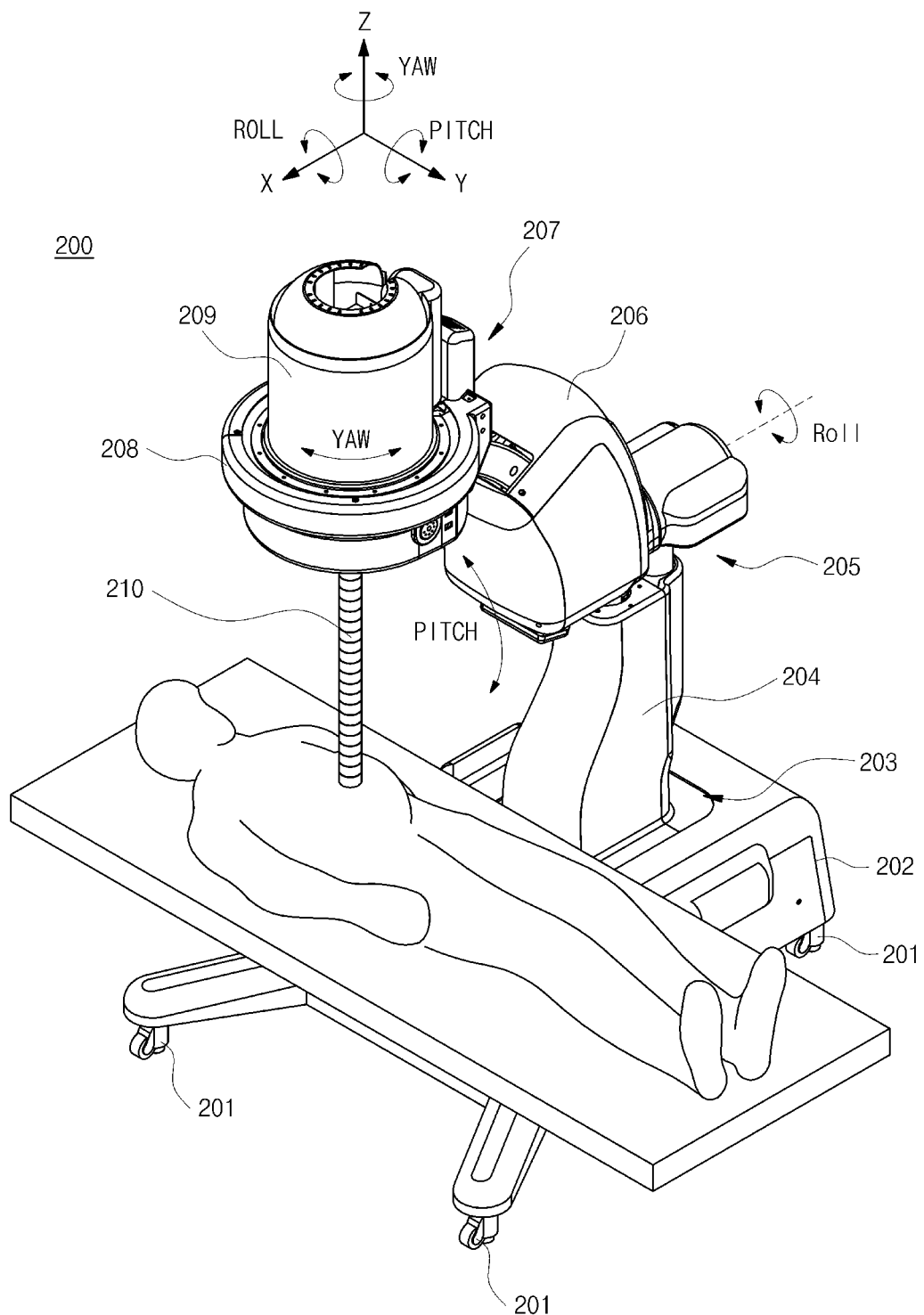
FIG. 2 is a perspective view illustrating the external appearance of a slave robot of the surgical robot in accordance with example embodiments.

FIG. 2 is a perspective view illustrating the external appearance of a slave robot of the surgical robot in accordance with example embodiments.

As shown in FIG. 2, the slave robot 200 includes a caster unit 201, a body 202, a robot arm 203~208, and a surgical instrument assembly 209.

The caster unit 201 serves to move the slave robot 200, and may be mounted at the lower part of the body 202. The caster unit 201 may include plural casters. Further, a lever (not shown) to change the operating state of each caster may be provided at each caster. The operator may change the operating states of the casters by adjusting the positions of the levers. The operating states of the casters may include a brake state, a free swivel state, and a directional lock (or swivel lock) state.

The robot arm 203~208 may be provided at the upper part of the body 202. The robot arm 203~208 may move the surgical instrument assembly 209 along at least one of the x-axis, the y-axis, and the z-axis, or rotate the surgical instrument assembly 209 about at least one of the x-axis, the y-axis, and the z-axis. Further, the robot arm 203~208 may support the surgical instrument assembly 209 so that the position and pose of the surgical instrument assembly 209 may be maintained during surgery.

The robot arm 203~208 may include plural link units 204, 206, and 208, and plural joint units 203, 205, and 207. In more detail, the robot arm 203~208 may include a first joint unit 203, a first link unit 204, a second joint unit 205, a second link unit 206, a third joint unit 207, and a third link unit 208.

The first link unit 204 may include a first link and a casing surrounding the first link. The first link may have a rectilinear column shape and be provided in the direction perpendicular to the body 202. That is, the first link may be provided in the direction perpendicular to the ground.

The first joint unit 203 is provided at the connection region between the body 202 and the first link unit 204. The first joint unit 203 may be implemented as a prismatic joint moving along a designated axis among the x-axis, the y-axis, and the z-axis. The first joint unit 203 serves to perform translational motion of the surgical instrument assembly 209, and has 3 DOF. In more detail, the first joint unit 203 has 3 DOF including x-axis translation, y-axis translation, and z-axis translation. For this purpose, the first joint unit 203 includes an x-axis translational drive unit, a y-axis translational drive unit, and a z-axis translational drive unit. Although not shown in FIG. 2, each translational drive unit may include a linear motion guide guiding linear motion along a specific axis and a motor providing driving force to the linear motion guide.

The second link unit 206 is provided at the front end of the first link unit 204. The second link unit 206 includes a second link and a casing surrounding the second link. The second link has a curved shape. In more detail, the second link has a shape of a part of an arc.

The second joint unit 205 is provided at the connection region between the first link unit 204 and the second link unit 206. The second joint unit 205 may be implemented as a revolute joint rotating about a designated axis among the x-axis, the y-axis, and the z-axis. The second joint unit 205 serves to perform rotary motion of the surgical instrument assembly 209, and has 2 DOF. In more detail, the second joint unit 205 has 2 DOF including rotation of the surgical instrument assembly 209 in the roll direction and rotation of the surgical instrument assembly 209 in the pitch direction. For this purpose, the second joint unit 205 may include a roll drive unit and a pitch drive unit.

When driving force is provided to the roll drive unit, the second link unit 206 is rotated in the roll direction. As the second link unit 206 is rotated in the roll direction, the third link unit 208 and the surgical instrument assembly 209 provided at the front end of the second link are rotated in the roll direction. For example, the roll drive unit may be one of a motor, a vacuum pump, and a hydraulic pump.

The pitch drive unit may include an R guide guiding arc motion of the second link, and a motor providing driving force to the R guide. When the motor of the pitch drive unit is driven, the second link moves along the R guide. As a result, the third link unit 208 and the surgical instrument assembly 209 provided at the front end of the second link are rotated in the pitch direction.

The third link unit 208 is provided at the front end of the second link unit 206. The third link unit 208 may include a circular third link. The surgical instrument assembly 209 is provided on the third link.

The third joint unit 207 is provided at the connection region between the second link unit 206 and the third link unit 208. The third joint unit 207 may be implemented as a revolute joint rotating about a designated axis among the x-axis, the y-axis, and the z-axis. The third joint unit 207 serves to perform rotary motion of the surgical instrument assembly 209, and has 1 DOF. In more detail, the third joint unit 207 has 1 DOF including rotation of the surgical instrument assembly 209 in the yaw direction. For this purpose, the third joint unit 207 may include a yaw drive unit.

When driving force is provided to the yaw drive unit, the surgical instrument assembly 209 is rotated in the yaw direction. The yaw drive unit may be one of a motor, a vacuum pump, and a hydraulic pump.

The surgical instrument assembly 209 may include a cylindrical casing, plural robotic surgical instruments provided along the inner surface of the casing, and the guide tube 210. Further, the robotic surgical instruments may include an endoscope to capture an image of the inside of the abdominal cavity and surgical tools to resect, cauterize, and coagulate human body tissues. Among the plural robotic surgical instruments provided along the inner surface of the casing, at least one robotic surgical instrument selected by the operator may enter the abdominal cavity of a patient through the guide tube 210. A detailed description of the robotic surgical instruments will be given later with reference to FIG. 3.

The surgical instrument assembly 209 may be mechanically separated from the third link unit 208. If the surgical instrument assembly 209 is separated from the third link unit 208, it may be easy to replace a surgical tool or to disinfect a surgical tool used in surgery.

Figure 3:
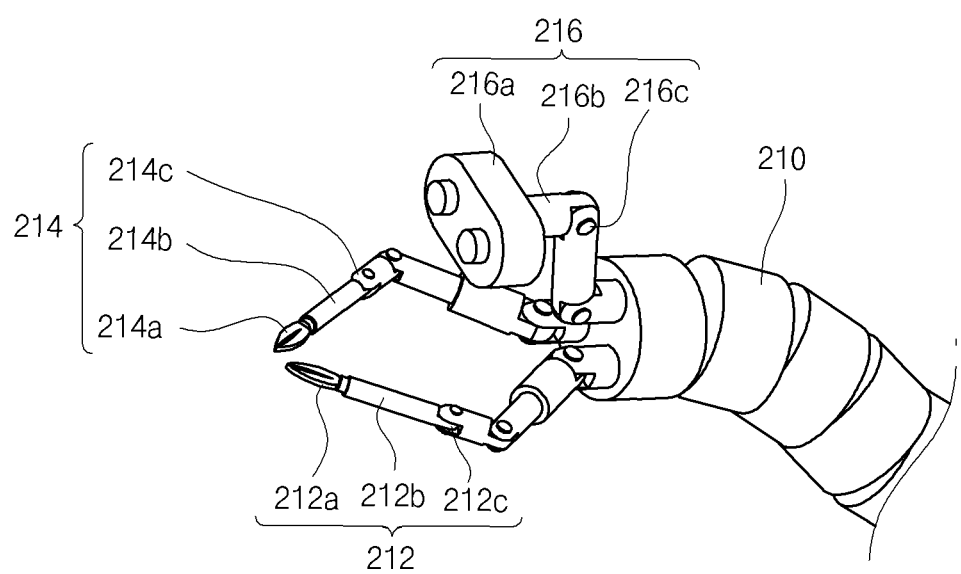
FIG. 3 is a view illustrating robotic surgical instruments spread through a guide tube in accordance with example embodiments.

FIG. 3 is a view illustrating the robotic surgical instruments 212, 214, and 216, spread through the guide tube 210 in accordance with example embodiments.

As described above, at least one robotic surgical instrument 212, 214, or 216 and 214 may enter into the abdominal cavity of a patient along the guide tube 210. Entry of the at least one robotic surgical instrument 212, 214, or 216 into the abdominal cavity of the patient may be performed through various methods. As one example, the guide tube 210 may be inserted into the abdominal cavity of the patient, and then movement of the guide tube 210 may be fixed. Next, the at least one robotic surgical instrument 212, 214, or 216 may be inserted into the guide tube 210, and then move along the inner wall of the guide tube 210. As another example, the at least one robotic surgical instrument 212, 214, or 216 may be inserted into the guide tube 210, and the guide tube 210 in such a state may enter into the abdominal cavity of a patient.

When the at least one robotic surgical instrument 212, 214, or 216 reaches a target position, the at least one robotic surgical instrument 212, 214, or 216 is spread to the outside of the guide tube 210, as shown in FIG. 3. FIG. 3 illustrates spreading of three robotic surgical instruments 212, 214, and 216 to the outside of the guide tube 210.

The respective robotic surgical instruments 212, 214, and 216 may include a plurality of links 212b, 214b, and 216b, and a plurality of joints 212c, 214c, and 216c.

An endoscope 216a and surgical tools 212a and 214a are provided at the tips of the respective links 212b, 214b, and 216b. The endoscope 216a and the surgical tools 212a and 214a may be understood as being end effectors of the slave robot 200.

The joints 212c, 214c, and 216c are provided between one link and another link. Each of the above-described joints 212c, 214c, and 216c may be one of a fixed joint, a revolute joint rotating about a designated axis among the x-axis, the y-axis, and the z-axis, and a prismatic joint linearly moving along a designated axis among the x-axis, the y-axis, and the z-axis. These joints 212c, 214c, and 216c may have 1 or more DOF.

A drive unit 170 (with reference to FIG. 5) may be provided at each of the joints 212c, 214c, and 216c of the robotic surgical instruments 212, 214, and 216. The drive unit 170 is driven according to a motion control signal received from the master console 100 and moves the corresponding joint. The drive unit 170 may be implemented as one of a motor, a vacuum pump, and a hydraulic pump. Hereinafter, the case in which a motor is used as the drive unit 170 will be described.

A detection unit 122, 124, and 126 (with reference to FIG. 5) may be provided at each of the joints 212c, 214c, and 216c of the robotic surgical instruments 212, 214, and 216. The detection unit 122, 124, and 126 may include a position detection unit 122 (with reference to FIG. 5) to detect the position of each joint (i.e., a joint angle), and a velocity detection unit 214 (with reference to FIG. 5) to detect the velocity of each joint.

The plural robotic surgical instruments 212, 214, and 216 may be controlled so as to follow motion of the handles 120L and 120R. However, control of the robotic surgical instrument 216 provided with the endoscope 216a and control of the robotic surgical instruments 212 and 214 provided with the surgical tools 212a and 214a may be divided according to operation mode switching of the surgical robot.

For example, if the endoscope operation mode is set as the operation mode of the surgical robot, the robotic surgical instrument 216 provided with the endoscope 216a is controlled so as to follow motion of the handles 120L and 120R. While the endoscope operation mode is performed, the robotic surgical instruments 212 and 214 provided with the surgical tools 212a and 214a may maintain the stopped state regardless of motion of the handles 120L and 120R.

If the surgical tool operation mode is set as the operation mode of the surgical robot, the robotic surgical instruments 212 and 214 provided with the surgical tools 212a and 214a are controlled so as to follow motion of the handles 120L and 120R. In more detail, the left robotic surgical instrument 212 is controlled so as to follow motion of the left handle 120L. The right robotic surgical instrument 214 is controlled so as to follow motion of the right handle 120R. While the surgical tool operation mode is performed, the robotic surgical instrument 216 provided with the endoscope 216a may maintain the stopped state regardless of motion of the handles 120L and 120R.

As above, the external appearances of the master console 100 and the slave robot 200 of the surgical robot have been described. Motion control and force control are performed with respect to each of the handles 120L and 120R and the robotic surgical instruments 212 and 214 in the disclosed surgical robot. Hereinafter, a more detailed description thereof will be given with reference to FIG. 4.

Figure 4:
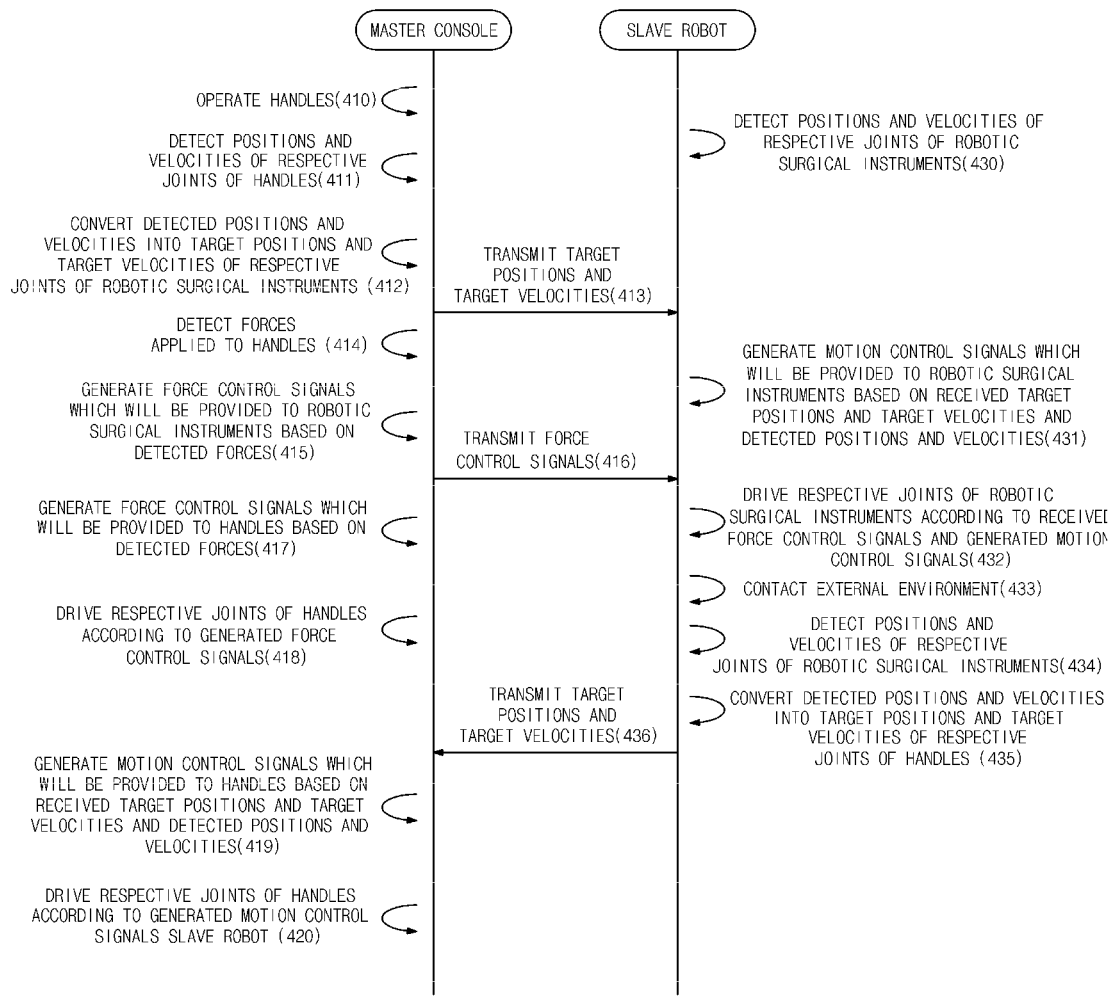
FIG. 4 is a conceptual diagram illustrating a control method of a surgical robot in accordance with example embodiments.

FIG. 4 is a conceptual diagram illustrating a control method of a surgical robot in accordance with example embodiments. Prior to description, it is assumed that the surgical tool operation mode is set as the operation mode of the surgical robot.

When the handles 120L and 120R are operated (Operation 410), the master console 100 detects positions and velocities of the respective joints of the operated handles 120L and 120R (Operation 411). Thereafter, the master console 100 converts the detected positions and velocities into target positions and target velocities which the respective joints of the robotic surgical instruments 212 and 214 will follow (Operation 412). The converted target positions and target velocities are transmitted to the slave robot 200 (Operation 413).

The slave robot 200 detects positions and velocities of the respective joints of the robotic surgical instruments 212 and 214 (Operation 430). Thereafter, the slave robot 200 generates motion control signals, which will be provided to the robotic surgical instruments 212 and 214, based on the target positions and target velocities received from the master console 100 and the positions and velocities detected by the slave robot 200 (Operation 431). Such motion control signals may be understood as being control signals to control the motion of the robotic surgical instruments 212 and 214 so as to follow motion of the handles 120L and 120R.

The master console 100 detects forces applied to the handles 120L and 120R (Operation 414). Thereafter, the master console 100 generates force control signals, which will be provided to the robotic surgical instruments 212 and 214, based on the forces detected in Operation 414 (Operation 415). In more detail, the master console 100 generates the force control signals, which will be provided to the robotic surgical instruments 212 and 214, by multiplying the forces detected in Operation 414 by a positive gain and then scaling acquired values by a predetermined or given scaling ratio. The generated force control signals are transmitted to the slave robot 200 (Operation 416).

Further, the master console 100 generates force control signals, which will be provided to the handles 120L and 120R, based on the forces detected in Operation 414 (Operation 417). In more detail, the master console 100 generates the force control signals, which will be provided to the handles 120L and 120R, by multiplying the forces detected in Operation 414 by a negative gain. The generated force control signals may be understood as being control signals to cancel out the forces applied to the handles 120L and 120R by the operator.

Thereafter, the master console 100 drives (moves or rotates) the respective joints of the handles 120L and 120R according to the force control signals generated in Operation 417 (Operation 418). As a result, the handles 120L and 120R are controlled so as to cancel out the forces applied to the handles 120L and 120R. When force control to cancel out the forces applied to the handles 120L and 120R is performed in such a manner, the operator does not feel forces applied to the handles 120L and 120R by the operator, while operating the handles 120L and 120R.

The reason why force control of the handles 120L and 120R is performed in such a manner is to achieve a correlation between forces received by the robotic surgical instruments 212 and 214 and forces felt by the operator through the handles 120L and 120R, if it is assumed that the robotic surgical instruments 212 and 214 move in the air.

In more detail, if it is assumed that the robotic surgical instruments 212 and 214 move in the air without any obstacle, the robotic surgical instruments 212 and 214 do not contact external environment and thus do not receive any force. Therefore, the operator operating the handles 120L and 120R should feel no force while the robotic surgical instruments 212 and 214 move in the air. As described above, when the force control signals are generated by multiplying the forces detected in Operation 414 by the negative gain and the respective joints of the handles 120L and 120R are operated according to the generated control signals, forces applied to the handles 120L and 120R by the operator are canceled out. As a result, the operator does not feel any force while operating the handles 120L and 120R.

The slave robot 200 drives (moves or rotates) the respective joints of the robotic surgical instruments 212 and 214 according to the force control signals received from the master console 100 in Operation 416 and the motion control signals generated by the slave robot 200 in Operation 431 (Operation 432). As a result, the robotic surgical instruments 212 and 214 follow motion of the handles 120L and 120R. In more detail, the positions and velocities of the end effectors 212a and 214a of the robotic surgical instruments 212 and 214 follow the positions and velocities of end effectors of the handles 120L and 120R.

Thereafter, the robotic surgical instruments 212 and 214 contact external environment (for example, tissues within the abdominal cavity) (Operation 433). Then, the slave robot 200 detects positions and velocities of the respective joints of the robotic surgical instruments 212 and 214 (Operation 434). Thereafter, the slave robot 200 converts the detected positions and velocities into target positions and target velocities which the respective joints of the handles 120L and 120R will follow (Operation 435). The converted target positions and target velocities are transmitted to the master console 100 (Operation 436).

The master console 100 generates motion control signals, which will be provided to the handles 120L and 120R, based on the target positions and target velocities received from the slave robot 200 and the positions and velocities detected by the master console 100 (Operation 419). In more detail, the master console 100 scales the target positions and target velocities received from the slave robot 200, and generates motion control signals, which will be provided to the handles 120L and 120R, based on the scaled target positions and target velocities and the positions and velocities detected by the master console 100.

Thereafter, the master console 100 drives (moves or rotates) the respective joints of the handles 120L and 120R according to the motion control signals generated in Operation 419 (Operation 420). As a result, the handles 120L and 120R follow motion of the robotic surgical instruments 212 and 214. In more detail, the positions and velocities of the end effectors of the handles 120L and 120R follow the positions and velocities of the end effectors 212a and 214a of the robotic surgical instruments 212 and 214.

If motion of the handles 120L and 120R is controlled so as to follow motion of the robotic surgical instruments 212 and 214 when the robotic surgical instruments 212 and 214 contact external environment, as described above, forces received by the robotic surgical instruments 212 and 214 from the external environment may be fed back to the handles 120L and 120R without provision of force/torque detection units in the robotic surgical instruments 212 and 214.

It may be similar to that, when an operator inserts a surgical tool of a manual laparoscopic surgical instrument into the abdominal cavity and performs surgery while holding an operating unit of the manual laparoscopic surgical instrument, the operator holding the operating unit of the manual laparoscopic surgical instrument feels force (reaction force) applied to the instrument, even if a sensor to detect force applied to the surgical tool due to contact with an organ within the abdominal cavity is not provided on the surgical tool.

The reason why the operator may feel force received by the surgical tool due to contact with an organ even if a sensor is not provided on the surgical tool of the manual laparoscopic surgical instrument is that the position of the surgical tool is moved little, as compared to force applied to the operating unit by the operator. That is, when force applied to the operating unit by the operator, the target position of the surgical tool moved according to the force applied by the operator, and the current position of the surgical tool after operation of the surgical tool according to the force applied by the operator are given, force received by the surgical tool due to contact with the organ may be estimated from a difference between the target position and the current position.

In the description of the disclosed surgical robot, the handles 120L and 120R are controlled so that the operator does not feel force through the handles 120L and 120R before the robotic surgical instruments 212 and 214 contact external environment, as described above. Simultaneously, the robotic surgical instruments 212 and 214 are controlled so as to follow motion of the handles 120L and 120R.

In such a state, when the robotic surgical instruments 212 and 214 receive force from the external environment, the slave robot 200 detects positions and velocities of the respective joints of the robotic surgical instruments 212 and 214. Then, the slave robot 200 converts the detected positions and velocities into target positions and target velocities which the respective joints of the handles 120L and 120R will follow, and transmits the converted target positions and target velocities to the master console 100.

The master console 100 compares the target positions and target velocities received from the slave robot 200 with the positions and velocities of the respective joints of the handles 120L and 120R detected by the master console 100. According to a comparison result, the master console 10 generates motion control signals to compensate for differences between the received target positions and the detected positions and/or differences between the received target velocities and the detected velocities. Thereafter, the master console 100 drives the respective joints of the handles 120L and 120R according to the generated motion control signals. As a result, the operator holding the handles 120L and 120R may indirectly feel forces received by the robotic surgical instruments 212 and 214 from the external environment.

In the above-described surgical robot, a motion equation of the master console 100 is stated as Equation 1 below. Among terms in Equation 1, terms having the subscript 'm' are terms relating to the master console 100, and terms having the subscript 's' are terms relating to the slave robot 200. Further, terms expressed by the mark '^' mean values detected by the force/torque detection units 126.

$$F_m = M_m a_m \quad \text{[Equation 1]}$$
$$= F_h - \hat{F}_h + M_m[k_p(x_s - x_m) + k_v(v_s - v_m)]$$

In Equation 1, $M_m$ means the mass of the handle 120L or 120R, and $a_m$ means the acceleration of the handle 120L or 120R. Further, $F_m$ means force applied to the handle 120L or 120R by the operator.

$\hat{F}_h$ means force detected by the force/torque detection unit 126. The reason why a negative (−) $\hat{F}_h$ is employed is that the handle 120L or 120R needs to be controlled so as to cancel out force applied to the handle 120L or 120R by the operator.

$x_s$ means the position of the end effecter 212a or 124a of the robotic surgical instrument 212 or 214. $x_s$ may be acquired by converting the positions of the respective joints of the robotic surgical instrument 212 or 214. $x_s$ may be understood as being target positions which the respective joints of the handle 120L or 120R will follow.)

$x_m$ means the position of the end effecter of the handle 120L or 120R. $x_m$ may be acquired by converting the positions of the respective joints of the handle 120L or 120R.

$v_s$ means the velocity of the end effecter 212a or 214a of the robotic surgical instrument 212 or 214. $v_s$ may be acquired by converting the velocities of the respective joints of the robotic surgical instrument 212 or 214. $v_s$ may be understood as being target velocities which the respective joints of the handle 120L or 120R will follow.

$v_m$ means the velocity of the end effecter of the handle 120L or 120R. $v_m$ may be acquired by converting the velocities of the respective joints of the handle 120L or 120R.

$k_p$ is a control gain required in position control, and $k_v$ is a control gain required in velocity control. $k_p$ and $k_v$ may be determined in advance through experimentation.

On the other hand, a motion equation of the slave robot 200 is stated as Equation 2 below. Among terms in Equation 2, terms having the subscript 'm' are terms relating to the master console 100, and terms having the subscript 's' are terms relating to the slave robot 200. Further, terms expressed by the mark '^' mean values detected by the force/torque detection units 126.

$$F_s = M_s a_s \qquad \text{[Equation 2]}$$
$$= \hat{F}_h - F_e + M_s[k_p(x_m - x_s) + k_v(v_m - v_s)]$$

In Equation 2, $M_s$ means the mass of the robotic surgical instrument 212 or 214, and $a_s$ means the acceleration of the robotic surgical instrument 212 or 214.

$\hat{F}_h$ means force detected by the force/torque detection unit 126 of the master console 100. Differing from Equation 1, the reason why a positive (+) $\hat{F}_h$ is employed is that the robotic surgical instrument 212 or 214 needs to be controlled according to force applied to the handle 120L or 120R by the operator.

$F_e$ means force received by the robotic surgical instrument 212 or 214 from external environment (for example, tissues within the abdominal cavity), if the robotic surgical instrument 212 or 214 contacts the external environment. The reason why a negative (−) $F_e$ is employed is that the direction of the force received by the robotic surgical instrument 212 or 214 from the external environment is opposite to the moving direction of the robotic surgical instrument 212 or 214.

$x_m$ means the position of the end effecter of the handle 120L or 120R. $x_m$ may be acquired by converting the positions of the respective joints of the handle 120L or 120R. $x_m$ may be understood as being target positions which the respective joints of the robotic surgical instrument 212 or 214 will follow.

$x_s$ means the position of the end effecter 212a or 214a of the robotic surgical instrument 212 or 214. $x_s$ may be acquired by converting the positions of the respective joints of the robotic surgical instrument 212 or 214.

$v_m$ means the velocity of the end effecter of the handle 120L or 120R. $v_m$ may be acquired by converting the velocities of the respective joints of the handle 120L and 120R. $v_m$ may be understood as being target velocities which the respective joints of the robotic surgical instrument 212 or 214 will follow.

$v_s$ means the velocity of the end effecter 212a or 214a of the robotic surgical instrument 212 or 214. $v_s$ may be acquired by converting the velocities of the respective joints of the robotic surgical instrument 212 or 214.

$k_p$ is a control gain required in position control, and $k_v$ is a control gain required in velocity control. $k_p$ and $k_v$ may be determined in advance through experimentation.

As stated above, control operation performed in the disclosed surgical robot has been generally described. Hereinafter, a control configuration of a surgical robot will be described, with reference to FIG. 5.

Figure 5:
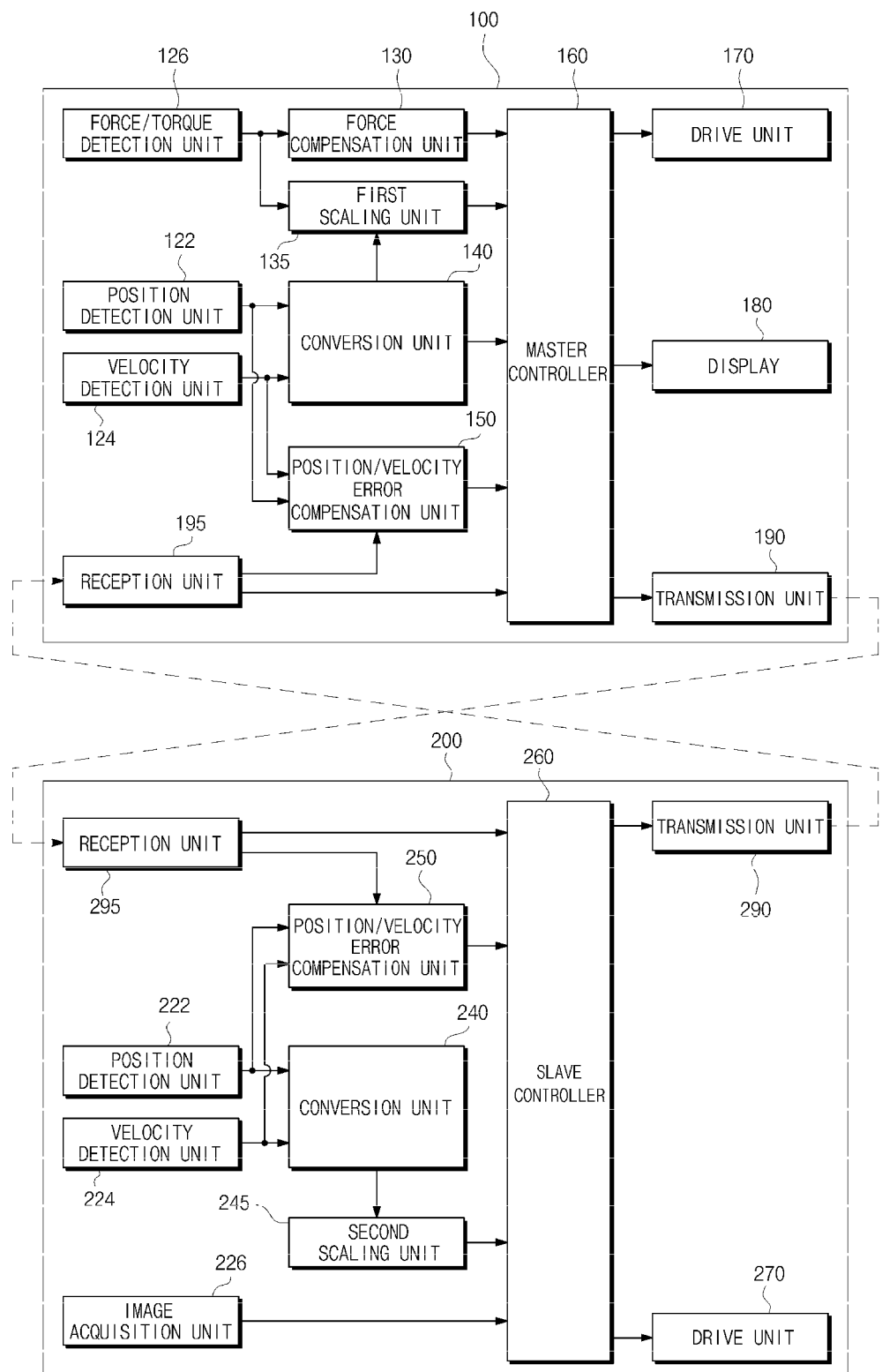
FIG. 5 is a block diagram illustrating a control configuration of a surgical robot in accordance with example embodiments.

FIG. 5 is a block diagram illustrating a control configuration of a surgical robot in accordance with example embodiments.

With reference to FIG. 5, the master console 100 may include force/torque detection units 126, position detection units 122, velocity detection units 124, a force compensation unit 130, a first scaling unit 135, a conversion unit 140, a position/velocity error compensation unit 150, a master controller 160, drive units 170, the displays 180, a transmission unit 190, and a reception unit 195.

The force/torque detection units 126 are provided on the handles 120L and 120R. For example, the force/torque detection units 126 may be provided at positions of the handles 120L and 120R corresponding to wrists of an operator. However, the force/torque detection units 126 are not limited to such positions, and may be provided at different positions of the handles 120L and 120R. For example, the force/torque detection units 126 may be provided at positions of the handles 120L and 120R corresponding to palms of the operator. The force/torque detection units 126 detect forces and/or torques applied to the handles 120L and 120R. For example, the force/torque detection units 126 may be implemented as force/torque sensors. Forces detected by the force/torque detection units 126 are respectively provided to the force compensation unit 130 and the first scaling unit 135, which will be described later.

The force compensation unit 130 generates force control signals to cancel out forces applied to the handles 120L and 120R by the operator by multiplying force values detected by the force/torque detection units 126 by a negative gain. The generated force control signals are provided to the master controller 160.

The position detection units 122 are provided at the handles 120L and 120R, i.e., the respective joints of the multi-joint fingers, and detect the positions of the respective joints. For example, the position detection units 122 may be implemented as position sensors. The position sensors may be potentiometers or encoders. The positions detected by the position detection units 122 are respectively provided to the conversion unit 140 and the position/velocity error compensation unit 150.

The velocity detection units 124 are provided at the handles 120L and 120R, i.e., the respective joints of the multi-joint fingers, and detect the velocities of the respective joints. For example, the velocity detection units 124 may be implemented as velocity sensors. The velocities detected by the velocity detection units 124 are respectively provided to the conversion unit 140 and the position/velocity error compensation unit 150.

Although FIG. 5 illustrates the master console 100 as including both the position detection units 122 and the velocity detection units 124, the velocity detection units 124 may be omitted as needed. If the velocity detection units 124 are omitted, velocity signals may be acquired by differentiating position signals detected by the position detection units 122. For this purpose, a velocity calculation unit (not shown) to calculate velocity signals by differentiating position signals detected by the position detection units 122 may be provided on the master console 100.

The conversion unit 140 converts the positions and velocities of the respective joints of the handles 120L and 120R into target positions and target velocities which the respective joints of the robotic surgical instruments 212 and 214 will follow. That is, the conversion unit 140 converts the positions and velocities detected by the position detection units 122 and the velocity detection units 124 into the target positions and target velocities which the respective joints of the robotic surgical instruments 212 and 214 will follow. For this purpose, the conversion unit 140 first converts the positions and velocities of the respective joints of the handles 120L and 120R into positions and velocities of the end effecters of the handles 120L and 120R. Next, the conversion unit 140 converts the positions and velocities of the end effecters of the handles 120L and 120R into target positions and target velocities of the respective joints of the robotic surgical instruments 212 and 214. The target positions and target velocities output from the conversion unit 140 are provided to the first scaling unit 135.

The first scaling unit 135 may scale data detected by the master console 100 by a predetermined or given scaling ratio.

As one example, the first scaling unit 135 generates force control signals, which will be transmitted to the slave robot 200, by scaling the force values detected by the force/torque detection units 126 by a predetermined or given scaling ratio. For this purpose, the first scaling unit 135 may apply a force scaling factor value to the detected force values.

For example, the force scaling factor value may be defined as '1/m' (here, m being a positive real number). Here, the force scaling factor value may be configured so as not to be changed or to be changed by the operator. If the force scaling factor value is configured so as to be changed by the operator, the operator may adjust the force scaling factor value by adjusting the value of m.

As one example, m may be set to a positive real number greater than 1. The force scaling factor value set in such a manner serves to reduce the force values detected by the force/torque detection units 126 by the predetermined or given ratio. As another example, m may be set to a positive real number less than 1. The force scaling factor value set in such a manner serves to enlarge the force values detected by the force/torque detection units 126 by the predetermined or given ratio.

When the force scaling factor value (1/m) is applied to the force values detected by the force/torque detection units 126 in such a manner, the operator may adjust a ratio between forces applied to the handles 120L and 120R and forces which will be provided to the robotic surgical instruments 212 and 214.

As another example, the first scaling unit 135 scales the target positions and target velocities output from the conversion unit 140 by a predetermined or given scaling ratio. For this purpose, the first scaling unit 135 may apply motion scaling factor values to the target positions and target velocities. For example, the motion scaling factor values may be defined as '1/n' (here, n being a positive real number). Here, the motion scaling factor values may be configured so as not to be changed or to be changed by the operator. If the motion scaling factor values are configured so as to be changed by the operator, the operator may adjust the motion scaling factor values by adjusting the value of n.

As one example, n may be set to a positive real number greater than 1. The motion scaling factor values set in such a manner serves to reduce the target positions and target velocities output from the conversion unit 140 by the predetermined or given ratio. As another example, n may be set to a positive real number less than 1. The motion scaling factor values set in such a manner serves to enlarge the target positions and target velocities output from the conversion unit 140 by the predetermined or given ratio.

According to example embodiments, the motion scaling factor value applied to the target positions and the motion scaling factor value applied to the target velocities may be equal or different.

When the motion scaling factor values (1/n) are applied to the target positions and target velocities output from the conversion unit 140 in such a manner, a ratio between motion of the robotic surgical instruments 212 and 214 and motion of the handles 120L and 120R may be adjusted. The target positions and target velocities scaled by the first scaling unit 135 are provided to the master controller 160.

The reception unit 195 is operated in pairs with a transmission unit 290 of the slave robot 200. The reception unit 195 receives image data and target positions and target velocities, which the respective joints of the handles 120L and 120R will follow, from the slave robot 200. The target positions and target velocities, which the respective joints of the handles 120L and 120R will follow, are output from a second scaling unit 245 of the slave robot 200.

The position/velocity error compensation unit 150 compares the target positions and target velocities received by the reception unit 195 and the positions and velocities detected by the position detection units 122 and the velocity detection units 124 of the master console 100. If there are differences between the received target positions and target velocities and the detected positions and velocities, the position/velocity error compensation unit 150 generates motion control signals to compensate for these differences. The generated motion control signals may be understood as being control signals to control motion of the handles 120L and 120R so as to follow motion of the robotic surgical instruments 212 and 214. The generated motion control signals are provided to the master controller 160.

The master controller 160 provides control signals to the drive units 170 provided at the respective joints of the handles 120L and 120R. In more detail, the master controller 160 provides the force control signals, provided from the force compensation unit 130, and the motion control signals, provided from the position/velocity error compensation unit 150, to the driving units 170.

Further, the master controller 160 provides data, which will be transmitted to the slave robot 200, to the transmission unit 190. In more detail, the master controller 160 provides the force control signals, scaled by the first scaling unit 135, and the target positions and target velocities, scaled by the first scaling unit 135, to the transmission unit 190.

Further, the master controller 160 may perform image processing of image data received through the reception unit 195. Image processing may include enlargement, reduction, movement, rotation, editing, and filtering of an acquired image. However, such image processing is not always performed by the master controller 160. Image processing by the master controller 160 may be omitted.

The drive units 170 may be provided at the respective joints of the handles 120L and 120R. In more detail, the drive units 170 may be provided at the respective joints of the multi-joint robot fingers. The drive units 170 are driven according to the force control signals and the motion control signals received from the master controller 160, and move or rotate the respective joints of the handles 120L and 120R. As a result, the handles 120L and the 120R are driven so as to cancel out forces applied to the handles 120L and 120R by the operator. Further, the handles 120L and 120R are driven so as to follow motion of the robotic surgical instruments 212 and 214.

The displays 180 may display image data. The image data may be image data received through the reception unit 195, or image data, image processing of which has been performed by the master controller 160.

The transmission unit 190 is operated in pairs with a reception unit 295 of the slave robot 200. The transmission unit 190 transmits data provided from the master controller 160, i.e., the force control signals scaled by the first scaling unit 135 and the target positions and target velocities scaled by the first scaling unit 135, to the slave robot 200.

Further, with reference to FIG. 5, the slave robot 200 may include position detection units 222, velocity detection units 224, an image acquisition unit 230, a conversion unit 240, a second scaling unit 245, a position/velocity error compensation unit 250, a slave controller 260, drive units 270, the transmission unit 290, and the reception unit 295.

The position detection units 222 are provided at the respective joints of the surgical instruments 212 and 214, and detect the positions of the respective joints. For example, the position detection units 222 may be implemented as position sensors. The position sensors may be potentiometers or encoders. The positions detected by the position detection units 222 are respectively provided to the conversion unit 240 and the position/velocity error compensation unit 250.

The velocity detection units 224 are provided at the respective joints of the surgical instruments 212 and 214, and detect the velocities of the respective joints. For example, the velocity detection units 224 may be implemented as velocity sensors. The velocities detected by the velocity detection units 224 are respectively provided to the conversion unit 240 and the position/velocity error compensation unit 250.

The velocity detection units 224 of the slave robot 200 may be omitted. In this case, velocity signals may be acquired by differentiating position signals detected by the position detection units 222. For this purpose, a velocity calculation unit (not shown) to calculate velocity signals by differentiating position signals detected by the position detection units 222 may be provided on the slave robot 200.

The conversion unit 240 converts the positions and velocities of the respective joints of the robotic surgical instruments 212 and 214, i.e., the positions and velocities detected by the position detection units 222 and the velocity detection units 224, into target positions and target velocities which the respective joints of the handles 120L and 120R will follow. For this purpose, the conversion unit 240 first converts the positions and velocities of the respective joints of the robotic surgical instruments 212 and 214 into positions and velocities of the end effecters 212a and 214a of the robotic surgical instruments 212 and 214. Next, the conversion unit 240 converts the positions and velocities of the end effecters 212a and 214a of the robotic surgical instruments 212 and 214 into target positions and target velocities of the respective joints of the handles 120L and 120R. The target positions and target velocities output from the conversion unit 240 are provided to the second scaling unit 245.

The second scaling unit 245 may scale data detected by the slave robot 200 in a predetermined or given scaling ratio.

As one example, the second scaling unit 245 scales the target positions and target velocities output from the conversion unit 240 by a predetermined or given scaling ratio. For this purpose, the second scaling unit 245 may apply motion scaling factor values to the target positions and target velocities output from the conversion unit 240. Here, the motion scaling facto values may be defined as the reciprocal numbers (n) of the motion scaling factors applied by the first scaling unit 135 of the master console 100. The target positions and target velocities scaled by the second scaling unit 245 are provided to the slave controller 260.

The reception unit 295 is operated in pairs with the transmission unit 190 of the master console 100. The reception unit 295 may receive data from the master console 100. For example, such data may be the force control signals, scaled by the first scaling unit 135, and the target positions and target velocities, scaled by the first scaling unit 135. The received force control signals are provided to the slave controller 260, and the received target positions and target velocities are provided to the position/velocity error compensation unit 250.

The position/velocity error compensation unit 250 compares the received target positions and target velocities and the positions and velocities detected by the position detection units 222 and the velocity detection units 224 of the slave robot 200. If there are differences between the received target positions and target velocities and the detected positions and velocities, the position/velocity error compensation unit 150 generates motion control signals to compensate for these differences. The generated motion control signals may be understood as being control signals to control motion of the robotic surgical instruments 212 and 214 so as to follow motion of the handles 120L and 120R. The generated motion control signals are provided to the slave controller 260.

The image acquisition unit 226 may acquire image data. For example, the image acquisition unit 226 may acquire image data by photographing the inside of the abdominal cavity of a patient. The image acquisition unit 226 may be understood as being the endoscope 216a shown in FIG. 3. The acquired image data may be provided to the slave controller 260.

The slave controller 260 provides control signals to the drive units 270 provided at the respective joints of the robotic surgical instruments 212 and 214. In more detail, the slave controller 260 provides the force control signals, provided from the reception unit 295, and the motion control signals, provided from the position/velocity error compensation unit 250, to the driving units 270.

Further, the slave controller 260 provides data, which will be transmitted to the master console 100, to the transmission unit 290. For example, such data may be the target positions and target velocities scaled by the second scaling unit 245.

Further, the slave controller 260 may perform image processing of image data acquired through the image acquisition unit 226. Image processing may include enlargement, reduction, movement, rotation, editing, and filtering of an acquired image. However, such image processing is not always performed by the slave controller 260. Image processing by the slave controller 260 may be omitted.

The drive units 270 may be provided at the respective joints of the robotic surgical instruments 212 and 214. The drive units 270 are driven according to the force control signals and the motion control signals provided from the slave controller 260, and move or rotate the respective joints of the robotic surgical instruments 212 and 214. As a result, motion of the robotic surgical instruments 212 and 214 are controlled so as to follow motion of the handles 120L and 120R. Further, the respective joints of the robotic surgical instruments 212 and 214 are controlled so as to follow forces applied to the handles 120L and 120R.

The transmission unit 290 is operated in pairs with the reception unit 195 of the master console 100. The transmission unit 290 transmits the target positions and target velocities, scaled by the second scaling unit 245, and/or image data to the master console 100.

As stated above, the control configuration of the surgical robot in accordance with example embodiments has been described with reference to FIG. 5. Hereinafter, surgical robots in accordance with other embodiments will be described with reference to FIGS. 6 to 8. Some constituent elements of the surgical robots in the embodiments shown in FIGS. 6 to 8 have similar functions to those of the surgical robot in the embodiment shown in FIG. 5, and a detailed description of these elements will thus be omitted.

Figure 6:
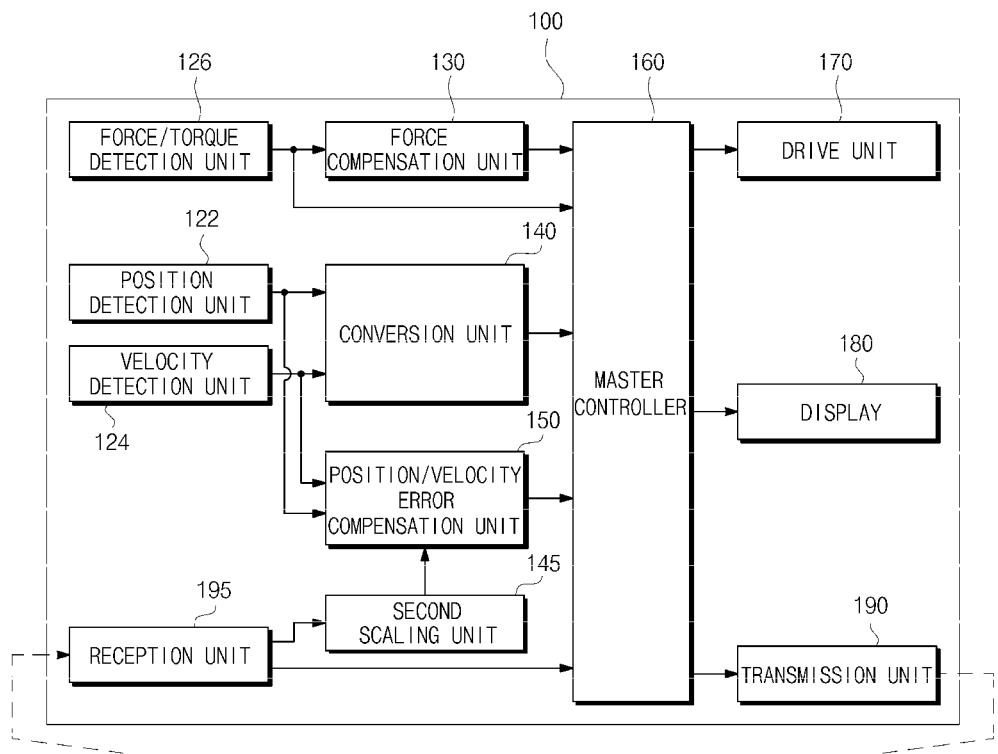
FIG. 6 is a block diagram illustrating a control configuration of a surgical robot in accordance with example embodiments.
Figure 6:
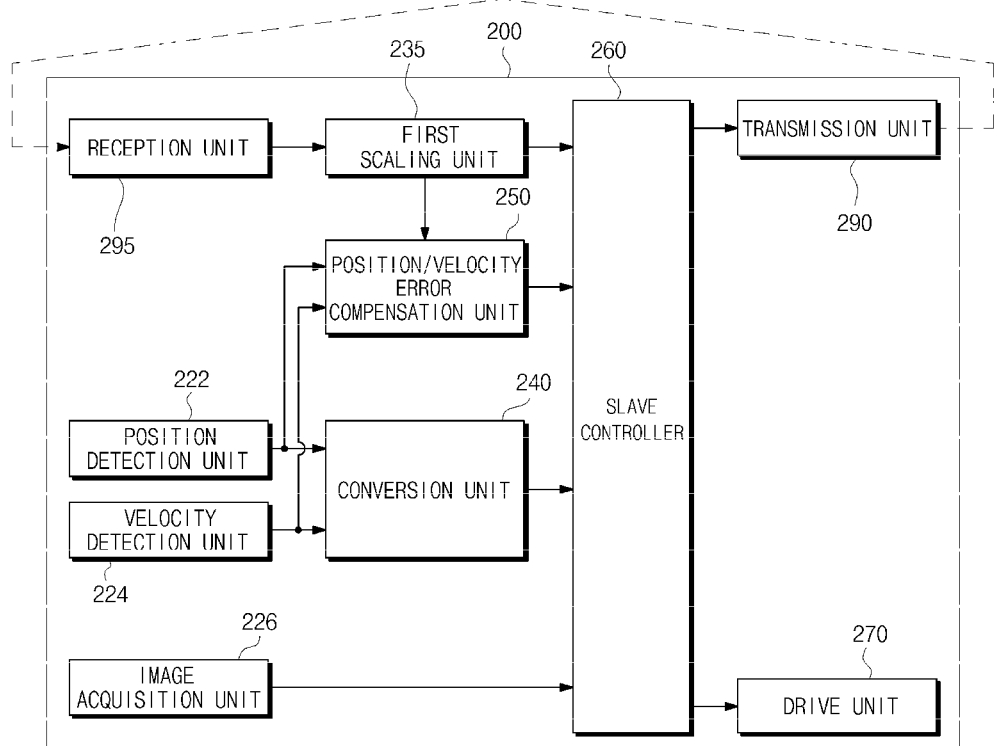

FIG. 6 is a block diagram illustrating a control configuration of a surgical robot in accordance with example embodiments.

The surgical robot shown in FIG. 6 differs from the surgical robot shown in FIG. 5 in that a second scaling unit 145 scaling data detected by a slave robot 200 by a predetermined or given scaling ratio is provided on a master console 100 and a first scaling unit 235 scaling data detected by the master console 100 by a predetermined or given scaling ratio is provided on the slave robot 200.

In this case, the master console 100 transmits force values, detected by force/torque detection units 126, and target positions and target velocities, output from a conversion unit 140, to the slave robot 200 without separate scaling.

Then, the first scaling unit 235 of the slave robot 200 scales the force values and the target positions and target velocities, received from the master console 100, by predetermined or given scaling ratios. In more detail, a force scaling factor value (1/m) is applied to the received force values. Further, motion scaling factor values (1/n) are applied to the received target positions and target velocities. The scaled force values are provided to a slave controller 260. Further, the scaled target positions and target velocities are provided to a position/velocity error compensation unit 250.

Further, the slave robot 200 transmits target positions and target velocities, output from a conversion unit 240, to the master console 100 without separate scaling.

Then, the second scaling unit 145 of the master console 100 scales the target positions and target velocities, received from the slave robot 200, by a predetermined or given scaling ratio. In more detail, motion scaling factor values (n) are applied to the received target positions and target velocities.

Figure 7:
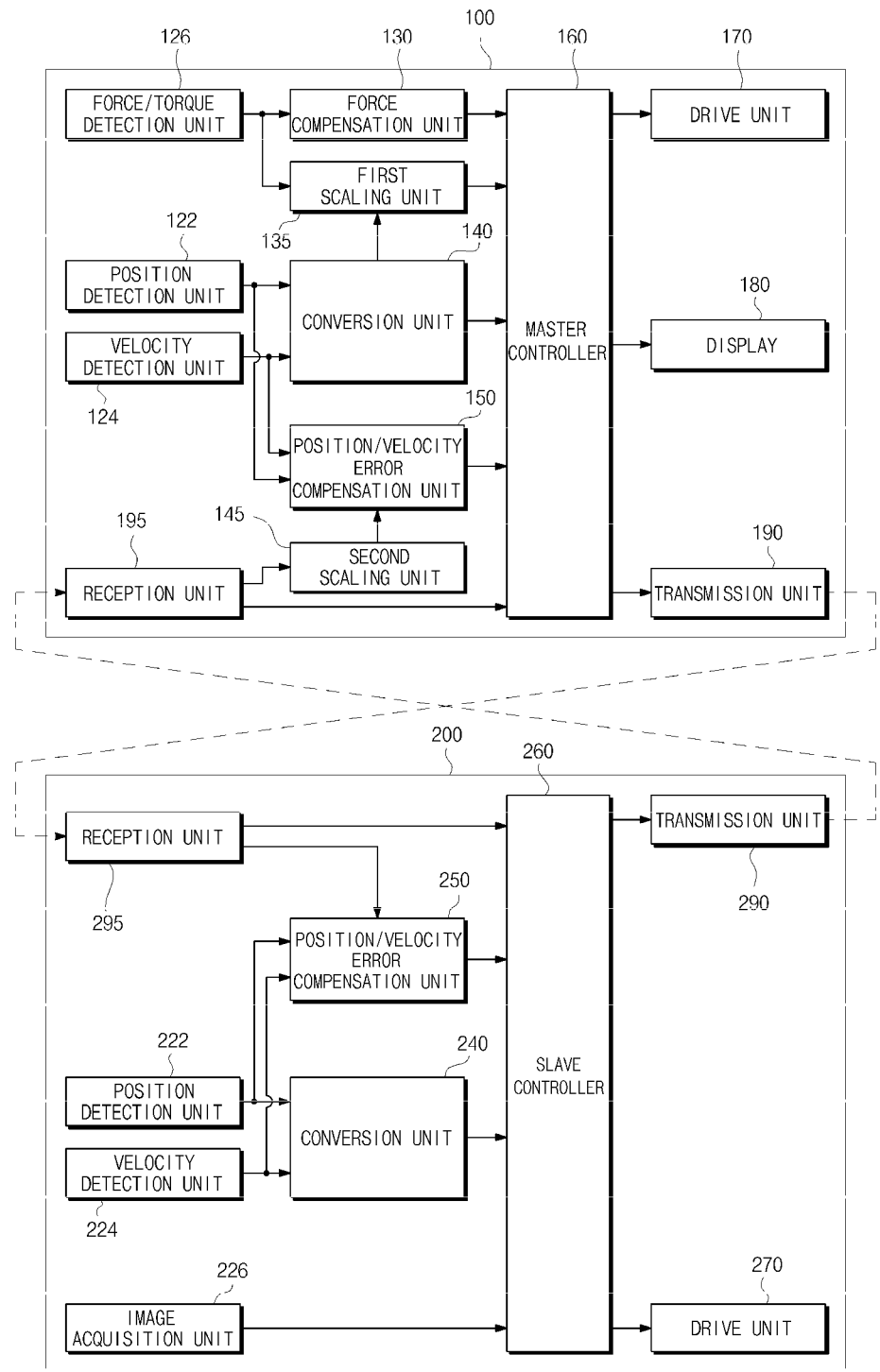
FIG. 7 is a block diagram illustrating a control configuration of a surgical robot in accordance with example embodiments.

FIG. 7 is a block diagram illustrating a control configuration of a surgical robot in accordance with example embodiments.

The surgical robot shown in FIG. 7 differs from the surgical robot shown in FIG. 5 in that both a first scaling unit 135 scaling data detected by a master console 100 in a predetermined or given scaling ratio and a second scaling unit 145 scaling data detected by a slave robot 200 by a predetermined or given scaling ratio are provided on the master console 100.

In this case, the first scaling unit 135 of the master console 100 scales force values, detected by force/torque detection units 126, and target positions and target velocities, output from a conversion unit 140, by predetermined or given scaling ratios. In more detail, a force scaling factor value (1/m) is applied to the received force values. Further, motion scaling factor values (1/n) are applied to the target positions and target velocities output from the conversion unit 140. The scaled force values and the scaled target positions and target velocities are provided to the slave robot 200.

A conversion unit 240 of the slave robot 200 converts positions and velocities, detected by position detection units 222 and velocity detection units 224, into target positions and target velocities which respective joints of handles 120L and 120R will follow. That is, the conversion unit 240 converts positions and velocities of respective joints of robotic surgical instruments 212 and 214 into the target positions and target velocities which the respective joints of the handles 120L and 120R will follow. Thereafter, the converted target positions and target velocities are transmitted to the master console 100 without separate scaling.

Then, the second scaling unit 145 of the master console 100 scales the target positions and target velocities, received from the slave robot 200, by a predetermined or given scaling ratio. In more detail, motion scaling factor values (n) are applied to the received target positions and target velocities. The scaled target positions and target velocities are provided to a position/velocity error compensation unit 150.

Figure 8:
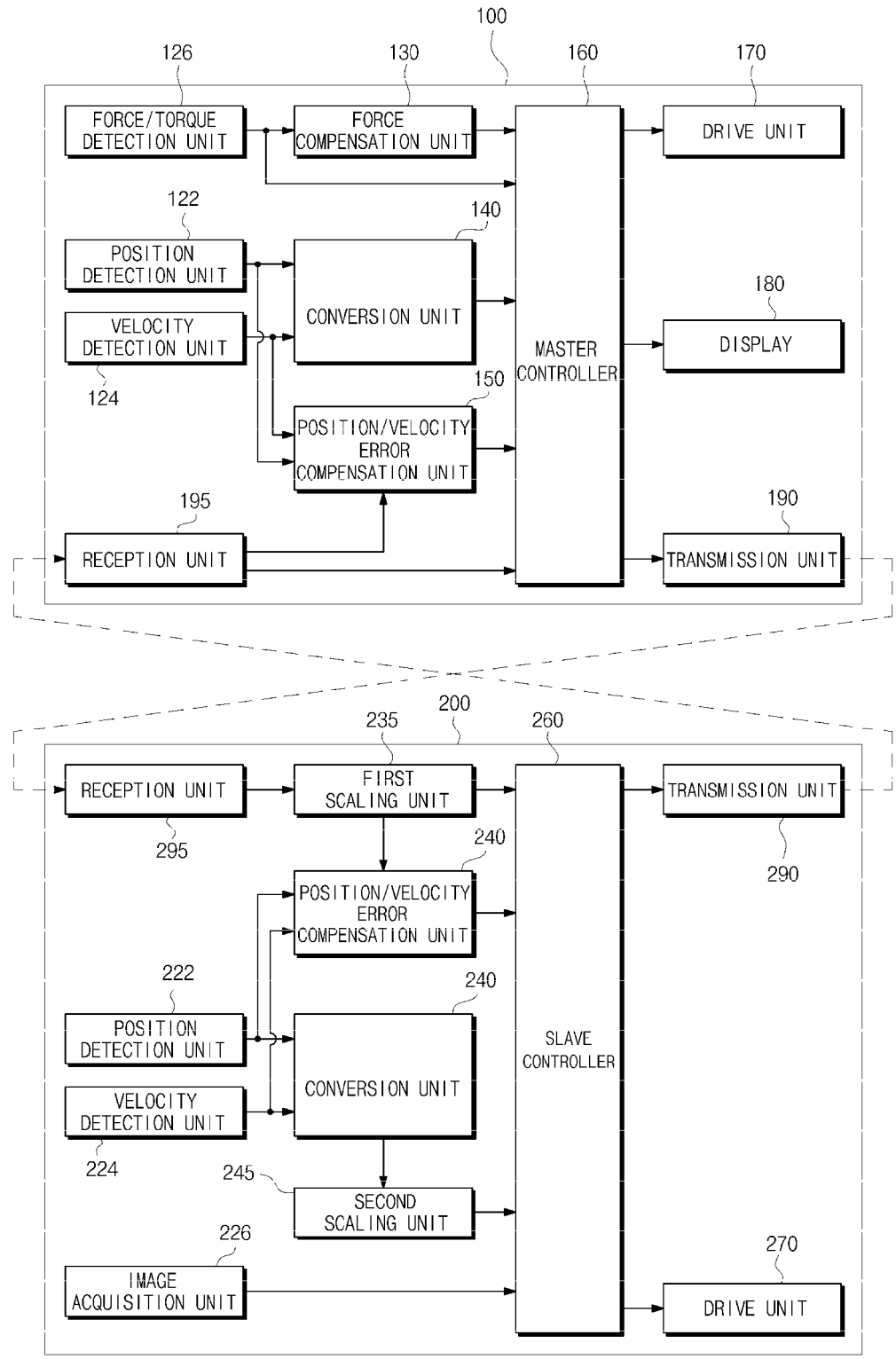
FIG. 8 is a block diagram illustrating a control configuration of a surgical robot in accordance with example embodiments.

FIG. 8 is a block diagram illustrating a control configuration of a surgical robot in accordance with example embodiments.

The surgical robot shown in FIG. 8 differs from the surgical robot shown in FIG. 5 in that both a first scaling unit 235 scaling data detected by a master console 100 by a predetermined or given scaling ratio and a second scaling unit 245 scaling data detected by a slave robot 200 by a predetermined or given scaling ratio are provided on the slave robot 200.

In this case, the master console 100 transmits force values, detected by force/torque detection units 126, and target positions and target velocities, output from a conversion unit 140, to the slave robot 200 without separate scaling.

Then, the first scaling unit 235 of the slave robot 200 scales the force values and the target positions and target velocities, received from the master console 100, by predetermined or given scaling ratios. In more detail, a force scaling factor value (1/m) is applied to the received force values. Further, motion scaling factor values (1/n) are applied to the received target positions and target velocities. The scaled force values are provided to a slave controller 260. Further, the scaled target positions and target velocities are provided to a position/velocity error compensation unit 250.

The second scaling unit 245 of the slave robot 200 scales the target positions and target velocities, output from a conversion unit 240, by a predetermined or given scaling ratio. In more detail, motion scaling factor values (n) are applied to the target positions and target velocities, output from the conversion unit 240. The scaled target positions and target velocities are provided to the master console 100.

As stated above, control configurations of surgical robots in accordance with embodiments have been described. In the disclosed surgical robots, forces received by the robotic surgical instruments 212 and 214 from external environment may be fed back to the handles 120L and 120R without provision of force/torque detection units in the robotic surgical instruments 212 and 214. As a result, an operator may indirectly feel the forces, received by the robotic surgical instruments 212 and 214 from the external environment, through the handles 120L and 120R.

Further, since the handles 120L and 120R and the robotic surgical instruments 212 and 214 are controlled by reflecting forces applied to the handles 120L and 120R by the operator, i.e., an operator intention, the robotic surgical instruments 212 and 214 may naturally follow motion of the handles 120L and 120R. A detailed description thereof will be given with reference to FIGS. 9 to 12(C).

FIG. 9 and FIGS. 10(A) to 10(C) are graphs illustrating simulation results of the disclosed surgical robot. In more detail, FIG. 9 and FIGS. 10(A) to 10(C) are graphs illustrating simulation results of the handle 120L or 120R and the robotic surgical instrument 212 or 214, if an operator performs a motion of drawing a circle using the handle 120L or 120R under the condition that an obstacle is located on a moving path of the robotic surgical instrument 212 or 214.

Figure 9:
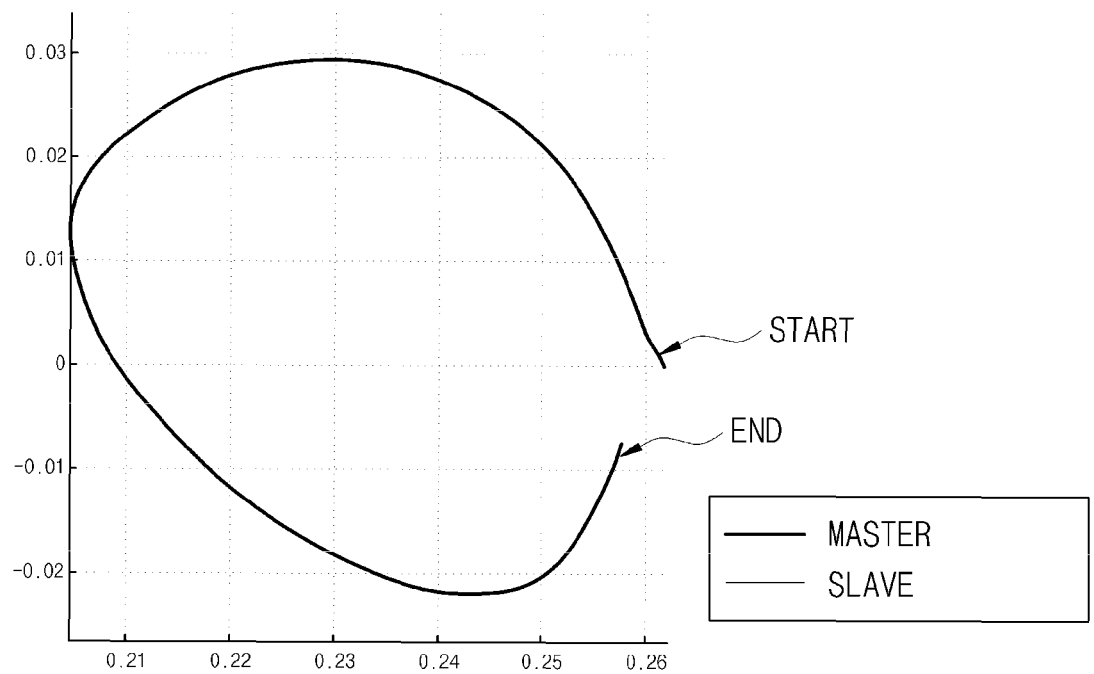
FIG. 9 is a graph illustrating a simulation result of the disclosed surgical robot, i.e., an xy trajectory of an end effecter of a handle and an xy trajectory of an end effecter of a robotic surgical instrument, if an operator performs a motion of drawing a circle using the handle under the condition that an obstacle is located on a moving path of the robotic surgical instrument.
Figure 10:
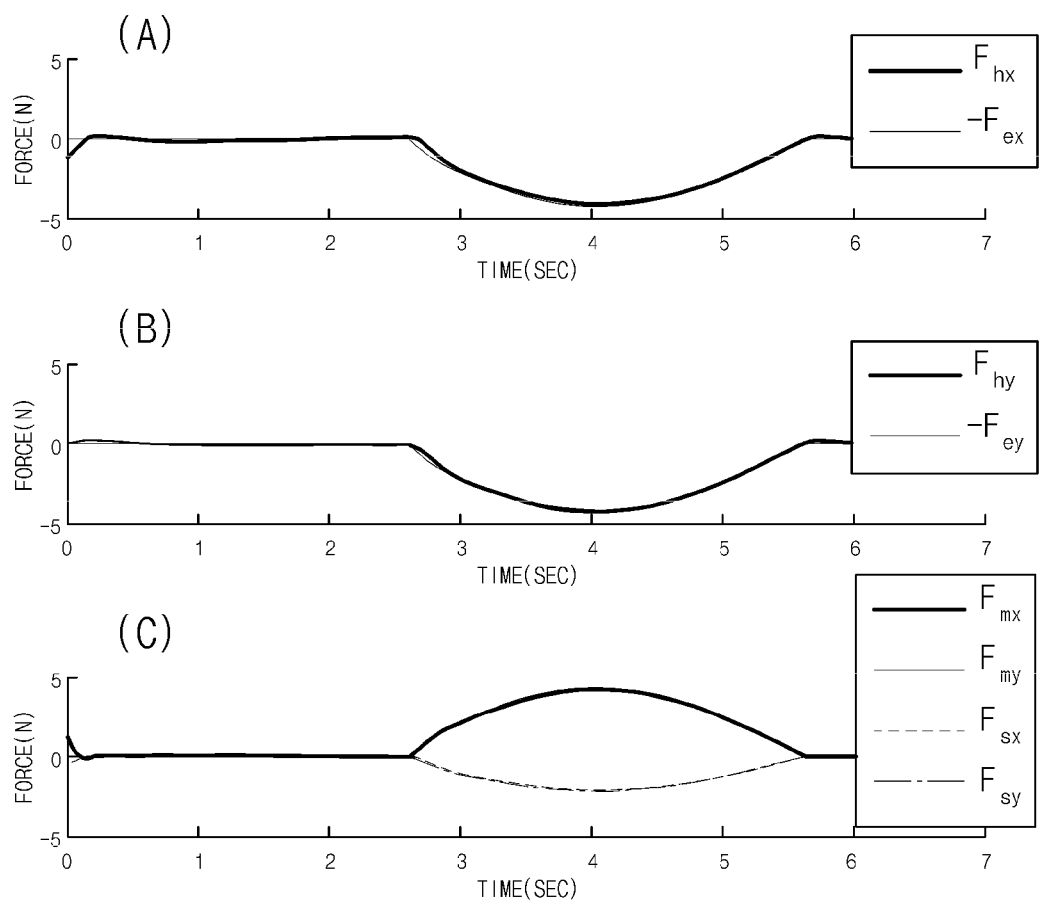
FIGS. 10(A) to 10(C) are graphs illustrating a simulation result of the disclosed surgical robot, i.e., changes of force applied to the handle by the operator, force applied to external environment (an obstacle) by the robotic surgical instrument, force acting on the handle, and force acting on the robotic surgical instrument, while such a motion is performed.

FIG. 9 is a graph illustrating an xy trajectory of the end effecter of the handle 120L or 120R and an xy trajectory of the end effecter 212a or 214a of the robotic surgical instrument 212 or 214, while such a motion is performed in the disclosed surgical robot.

In FIG. 9, a thick solid line represents a result measured by the master console 100. That is, the thick solid line represents the xy trajectory of the end effecter of the handle 120L or 120R. Further, a thin solid line represents a result measured by the slave robot 200. That is, the thin solid line represents the xy trajectory of the end effecter 212a or 214a of the robotic surgical instrument 212 or 214.

With reference to FIG. 9, it may be confirmed that the xy trajectory maintains an arc shape during a designated time from start of operation of the handle 120L or 120R and is distorted after the designated time. The reason for this is that the robotic surgical instrument 212 or 214 moves in the air during the designated time from start of operation of the handle 120L or 120R and contacts an obstacle after the designated time.

With reference to FIG. 9, it may be confirmed that the xy trajectory of the handle 120L or 120R and the xy trajectory of the robotic surgical instrument 212 or 214 almost coincide with each other until operation of the handle 120L or 120R is ended after start of operation of the handle 120L or 120R. From such a result, it may be confirmed that the robotic surgical instrument 212 or 214 follows motion of the handle 120L or 120R before the end effecter 212a or 214a of the robotic surgical instrument 212 or 214 contacts an obstacle after start of operation of the handle 120L or 120R. Further, it may be confirmed that the robotic surgical instrument 212 or 214 follows motion of the handle 120L or 120R even while the robotic surgical instrument 212 or 214 contacts an obstacle.

FIGS. 10(A) to 10(C) are graphs illustrating changes of force felt by the operator through the handle 120L or 120R, force applied to the robotic surgical instrument 212 or 214 by external environment (an obstacle), force output from the handle 120L or 120R, and force output from the robotic surgical instrument 212 or 214, while such a motion is performed in the disclosed surgical robot.

In the graphs shown in FIGS. 10(A) to 10(C), the horizontal axis represents time and the vertical axis represents force. With reference to FIGS. 10(A) to 10(C), it may be confirmed that force is not changed in a section from 0 to about 2.7 seconds and is then changed in a section from about 2.7 to about 5.7 seconds. The reason for this is that the robotic surgical instrument 212 or 214 moves in the air in the section from 0 to about 2.7 seconds and contacts an obstacle in the section from about 2.7 to about 5.7 seconds. Hereinafter, the graphs shown in FIGS. 10(A) to 10(C) will be described in more detail.

In FIG. 10(A), a thick solid line represents force ($F_{hx}$) in the x-axis direction felt by the operator through the handle 120L or 120R. A thin solid line represents force ($-F_{ex}$) in the x-axis direction applied to the robotic surgical instrument 212 or 214 by external environment. The force ($-F_{ex}$) in the x-axis direction applied to the robotic surgical instrument 212 or 214 by the external environment is measured by a sensor provided in the external environment.

With reference to FIG. 10(A), it may be confirmed that, both when the robotic surgical instrument 212 or 214 moves in the air and when the robotic surgical instrument 212 or 214 contacts the external environment, the force ($F_{hx}$) in the x-axis direction felt by the operator through the handle 120L or 120R and the force ($-F_{ex}$) in the x-axis direction applied to the robotic surgical instrument 212 or 214 by the external environment almost coincide with each other. Such a result means that the force applied to the robotic surgical instrument 212 or 214 by the external environment is effectively transmitted to the handle 120L or 120R even while the robotic surgical instrument 212 or 214 contacts the external environment. That is, it means that the operator effectively feels the force, applied to the robotic surgical instrument 212 or 214 by the external environment, through the handle 120L or 120R.

In FIG. 10(B), a thick solid line represents force ($F_{hy}$) in the y-axis direction felt by the operator through the handle 120L or 120R. A thin solid line represents force ($-F_{ey}$) in the y-axis direction applied to the robotic surgical instrument 212 or 214 by the external environment. The force ($-F_{ey}$) in the y-axis direction applied to the robotic surgical instrument 212 or 214 by the external environment is measured by a sensor provided in the external environment.

With reference to FIG. 10(B), it may be confirmed that, both when the robotic surgical instrument 212 or 214 moves in the air and when the robotic surgical instrument 212 or 214 contacts the external environment, the force ($F_{hy}$) in the y-axis direction felt by the operator through the handle 120L or 120R and the force ($-F_{ey}$) in the y-axis direction applied to the robotic surgical instrument 212 or 214 by the external environment almost coincide with each other. Such a result means that the force applied to the robotic surgical instrument 212 or 214 by the external environment is effectively transmitted to the handle 120L or 120R even while the robotic surgical instrument 212 or 214 contacts the external environment.

In FIG. 10(C), a thick solid line represents force ($F_{mx}$) in the x-axis direction output from the handle 120L or 120R. A thin solid line represents force ($F_{my}$) in the y-axis direction output from the handle 120L or 120R. A dashed line represents force ($F_{sx}$) in the x-axis direction output from the robotic surgical instrument 212 or 214. An alternating long and short dash line represents force ($F_{sy}$) in the y-axis direction output from the robotic surgical instrument 212 or 214.

In FIG. 10(C), it is assumed that a line interconnecting points having a force value of 0 according to time is defined as a reference line. In this case, it may be confirmed that the shape of the forces ($F_{mx}$, $F_{my}$) output from the handle 120L or 120R and the shape of forces ($F_{sx}$, $F_{sy}$) felt by the operator are almost symmetrical with respect to the reference line. From such a result, it may be confirmed that the forces ($F_{mx}$, $F_{my}$) output from the handle 120L or 120R and the forces ($F_{sx}$, $F_{sy}$) felt by the operator almost coincide with each other.

FIG. 11 and FIGS. 12(A) to 12(C) are graphs illustrating simulation results of a conventional surgical robot. In more detail, FIG. 11 and FIGS. 12(A) to 12(C) are graphs illustrating simulation results of a handle and a robotic surgical instrument, if an operator performs a motion of drawing a circle using the handle under the condition that an obstacle is located on a moving path of the robotic surgical instrument.

Figure 11:
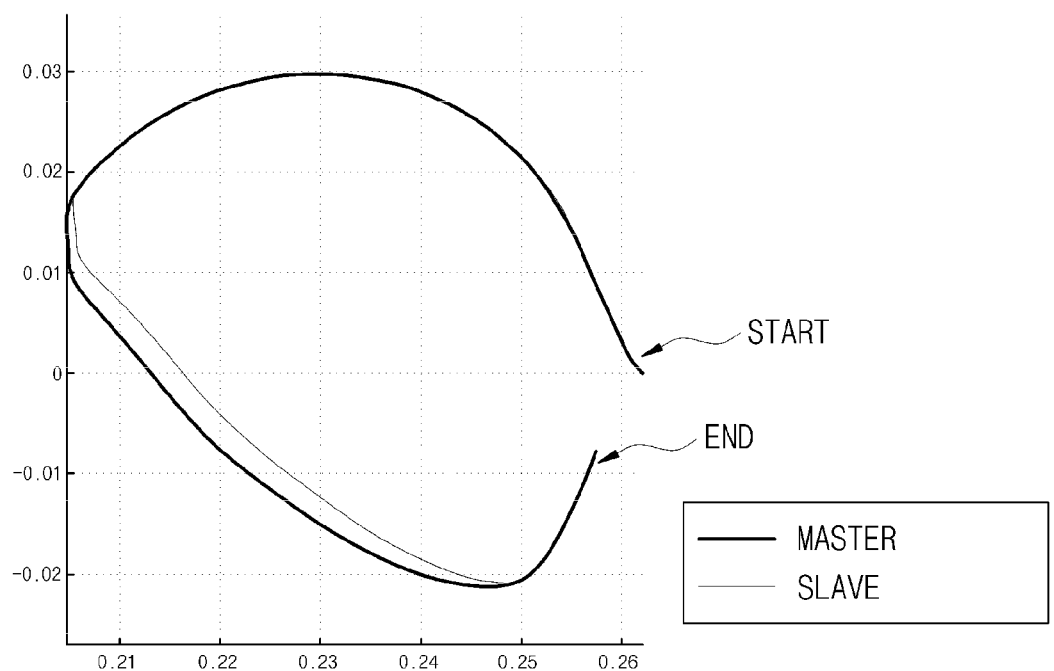
FIG. 11 is a graph illustrating a simulation result of a conventional surgical robot, i.e., an xy trajectory of an end effecter of a handle and an xy trajectory of an end effecter of a robotic surgical instrument, while such a motion is performed.
Figure 12:
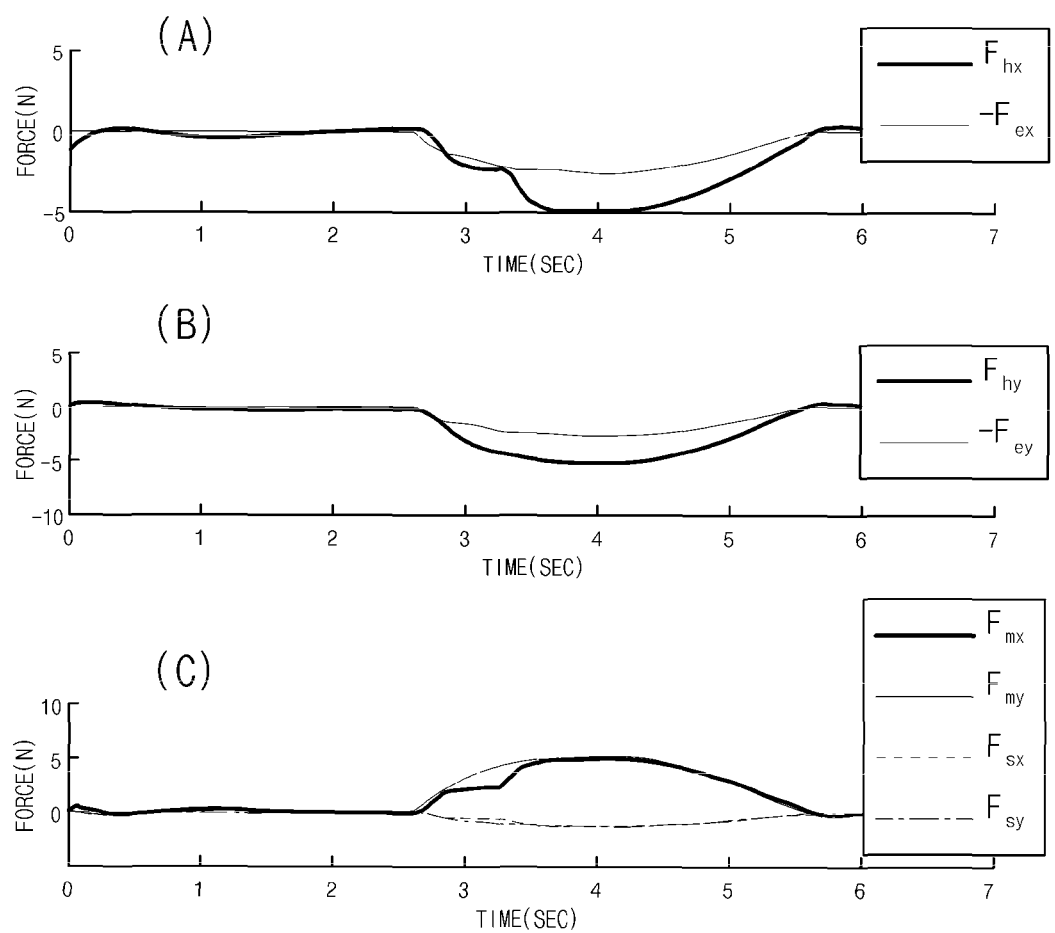
FIGS. 12(A) to 12(C) are graphs illustrating a simulation result of the conventional surgical robot, i.e., changes of force applied to the handle by the operator, force applied to external environment (an obstacle) by the robotic surgical instrument, force acting on the handle, and force acting on the robotic surgical instrument, while such a motion is performed.

FIG. 11 is a graph illustrating an xy trajectory of an end effecter of the handle and an xy trajectory of an end effecter of the robotic surgical instrument, while such a motion is performed in the conventional surgical robot.

In FIG. 11, a thick solid line represents a result measured by a master console. That is, the thick solid line represents the xy trajectory of the end effecter of the handle. Further, a thin solid line represents a result measured by a slave robot. That is, the thin solid line represents the xy trajectory of the end effecter of the robotic surgical instrument.

With reference to FIG. 11, it may be confirmed that the xy trajectory of the end effecter of the handle and the xy trajectory of the end effecter of the robotic surgical instrument almost coincide with each other before the robotic surgical instrument contacts an obstacle after start of operation of the handle. That is, it may be confirmed that the robotic surgical instrument is controlled so as to follow motion of the handle. However, it may be confirmed that the xy trajectory of the end effecter of the handle and the xy trajectory of the end effecter of the robotic surgical instrument are different while the robotic surgical instrument contacts an obstacle.

FIGS. 12(A) to 12(C) are graphs illustrating changes of force felt by the operator through the handle, force applied to the robotic surgical instrument by external environment (an obstacle), force output from the handle, and force output from the robotic surgical instrument, while such a motion is performed in the conventional surgical robot.

In the graphs shown in FIGS. 12(A) to 12(C), the horizontal axis represents time and the vertical axis represents force. With reference to FIGS. 12(A) to 12(C), it may be confirmed that force is not changed in a section from 0 to about 2.7 seconds and is then changed in a section from about 2.7 to about 5.7 seconds. The reason for this is that the robotic surgical instrument moves in the air in the section from 0 to about 2.7 seconds and contacts an obstacle in the section from about 2.7 to about 5.7 seconds. Hereinafter, the graphs shown in FIGS. 12(A) to 12(C) will be described in more detail.

In FIG. 12(A), a thick solid line represents force ($F_{hx}$) in the x-axis direction felt by the operator through the handle. A thin solid line represents force ($-F_{ex}$) in the x-axis direction applied to the robotic surgical instrument by external environment.

With reference to FIG. 12(A), it may be confirmed that, while the robotic surgical instrument moves in the air, the force ($F_{hx}$) in the x-axis direction felt by the operator through the handle and the force ($-F_{ex}$) in the x-axis direction applied to the robotic surgical instrument by the external environment almost coincide with each other. However, it may be confirmed that, while the robotic surgical instrument contacts the external environment, the force ($F_{hx}$) in the x-axis direction felt by the operator through the handle and the force ($-F_{ex}$) in the x-axis direction applied to the robotic surgical instrument by the external environment are remarkably different. Such a result means that the force applied to the robotic surgical instrument by the external environment is not effectively transmitted to the handle while the robotic surgical instrument contacts the external environment.

In FIG. 12(B), a thick solid line represents force ($F_{hy}$) in the y-axis direction felt by the operator through the handle. A thin solid line represents force ($-F_{ey}$) in the y-axis direction applied to the robotic surgical instrument by the external environment.

With reference to FIG. 12(B), it may be confirmed that, while the robotic surgical instrument moves in the air, the force ($F_{hy}$) in the y-axis direction felt by the operator through the handle and the force ($-F_{ey}$) in the y-axis direction applied to the robotic surgical instrument by the external environment almost coincide with each other. However, it may be confirmed that, while the robotic surgical instrument contacts the external environment, the force ($F_{hy}$) in the y-axis direction felt by the operator through the handle and the force ($-F_{ey}$) in the y-axis direction applied to the robotic surgical instrument by the external environment are remarkably different. Such a result means that the force applied to the robotic surgical instrument by the external environment is not effectively transmitted to the handle while the robotic surgical instrument contacts the external environment.

In FIG. 12(C), a thick solid line represents force ($F_{mx}$) in the x-axis direction output from the handle. A thin solid line represents force ($F_{my}$) in the y-axis direction output from the handle. A dashed line represents force ($F_{sx}$) in the x-axis direction output from the robotic surgical instrument. An alternating long and short dash line represents force ($F_{sy}$) in the y-axis direction output from the robotic surgical instrument.

Although not shown in FIG. 12(C), it is assumed that a line interconnecting points having a force value of 0 according to time is defined as a reference line. In this case, it may be confirmed that the shape of the forces ($F_{mx}$, $F_{my}$) output from the handle and the shape of forces ($F_{sx}$, $F_{sy}$) felt by the operator are almost asymmetrical with respect to the reference line. From such a result, it may be confirmed that the forces ($F_{mx}$, $F_{my}$) output from the handle and the forces ($F_{sx}$, $F_{sy}$) felt by the operator are different.

Through comparison between FIGS. 10(A) to 10(C) and FIGS. 12(A) to 12(C), it may be confirmed that force feedback between the handles 120L and 120R and the robotic surgical instruments 212 and 214 of the disclosed surgical robot is effectively performed, as compared to the conventional surgical robot.

In the above-described embodiments, some of the elements of the master console 100 and the slave robot 200 may be implemented as a kind of 'module'. For example, at least one of the force compensation unit 130, the first scaling unit 135 or 235, the second scaling unit 145 or 245, the conversion units 140 and 240, the position/velocity error compensation units 150 and 250, the master controller 160, and the slave controller 260 may be implemented as a module.

Here, "module" means a software-based component or a hardware component, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components, such as software components, object-oriented software components, class components, and task components, processes, functions, attributes, procedures, subroutines, segments of program codes, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more CPUs in a device.

Some example embodiments may be implemented through a medium including computer readable codes/instructions to control at least one processing element of the above-described embodiment, for example, a computer readable medium. Such a medium may correspond to a medium/media which may store and/or transmit the computer readable codes.

The computer readable codes may be recorded in a medium or be transmitted over the Internet. For example, the medium may include a ROM, a RAM, a CD-ROM, a magnetic tape, a floppy disk, an optical recording medium, or a carrier wave, e.g., data transmission over the Internet. Further, the medium may be a non-transitory computer readable medium. Since the medium may be a distributed network, the computer readable code may be stored, transmitted and executed in a distributed manner. Further, for example, the processing element may include a processor or a computer processor, and be distributed and/or included in one device.

As is apparent from the above description, a surgical robot and a control method thereof in accordance with example embodiments may feed force, received by a robotic surgical instrument due to contact with external environment, back to a master console without provision of a force/torque sensor in the robotic surgical instrument, thus providing realism to an operator of the master console.

The surgical robot and the control method thereof do not require the force/torque sensor provided in the robotic surgical instrument, thus not requiring size reduction of the force/torque sensor according to size reduction of the robotic surgical instrument.

The surgical robot and the control method thereof do not require the size-reduced force/torque sensor, thus preventing or reducing instability of the surgical robot due to noise generated from the size-reduced force/torque sensor.

The surgical robot and the control method thereof do not require the force/torque sensor provided in the robotic surgical instrument, thus being advantageous in terms of costs, as compared to the case in which a robotic surgical instrument provided with a force/torque sensor is discarded.

Although a few example embodiments have been shown and described, it would be appreciated by those skilled in the art that changes may be made in these embodiments without departing from the principles and spirit of the claims and their equivalents. For example, while certain operations have been described as being performed by the controller associated with the master console 100 or the slave robot 200, one of ordinary skill in the art will appreciate that the operations may be divided between the controllers in various manners. For example, the operations discussed as being performed by the controllers may be segmented between controllers of a plurality of master consoles 100 and a plurality of slave robots 200. Further, various operations discussed as being performed by the controller of the master console 100 may be performed by the controller of the slave robot 200, and vice versa.

Additionally, while example embodiments have been described with relation to a surgical robot, one of ordinary skill in the art will appreciate that the example embodiments may be applied to extend the working space of various other robot systems. For example, robotic systems for use in various manufacturing industries. Likewise, in such embodiments, the surgical tools described herein as being attached to the guide tube may be replaced with various tools other than surgical tools. For example, tools utilized in various manufacturing industries. Examples of various tools may include hand tools (e.g., a hammer, anvil, chisel, etc.) and electronic tools (e.g., a welder, torch, etc.).

What is claimed is:

1. A master console of a surgical robot comprising:
   handles configured to control robotic surgical instruments of a slave robot;
   force/torque detectors configured to detect forces applied to the handles by an operator;
   a force compensator configured to generate force control signals by multiplying the forces detected by the force/torque detectors by a negative gain; and
   a master controller configured to drive at least one joint of each of the handles based on the generated force control signals and motion control signals controlling motion of the handles;
   a position/velocity error compensator configured to generate the motion control signals in order to compensate for differences between a position and a velocity of the at least one joint of each of the handles and a target position and a target velocity for the at least one joint of each of the handles based on target position and velocity values input via the handles,
   the target position and the target velocity are determined from a position and a velocity of an end effector of each of the robotic surgical instruments, and
   the position and the velocity of the end effector of each of the robotic surgical instruments are determined from a position and a velocity of the at least one joint of each of the robotic instruments.

2. The master console according to claim 1, wherein the target position and the target velocity are scaled by a scaling ratio.

3. The master console according to claim 1, wherein the master console transmits the forces detected by the force/torque detectors and a target position and a target velocity for the at least one joint of each of the robotic surgical instruments to the slave robot.

4. The master console according to claim 3, wherein:
   the target position and the target velocity are determined from a position and a velocity of an end effector of each of the handles; and
   the position and the velocity of the end effector of each of the handles are determined from a position and a velocity of the at least one joint of each of the handles.

5. The master console according to claim 3, wherein the detected forces and the target position and the target velocity are scaled by respective scaling ratios.

6. The master console according to claim 5, wherein the slave robot is configured to generate the motion control signals in order to compensate for differences between a position and a velocity and the scaled target position and target velocity of the at least one joint of each of the robotic surgical instruments, and is configured to drive the at least one joint of each of the robotic surgical instruments based on the generated motion control signals and the scaled forces.

7. A surgical robot comprising:
   a slave robot including robotic surgical instruments; and
   a master console configured to detect forces applied to handles by an operator in order to control the robotic surgical instruments of the slave robot, configured to generate force control signals by multiplying the forces detected by force/torque detectors by a negative gain, and configured to drive at least one joint of each of the handles based on motion control signals controlling motion of the handles and the force control signals,
   wherein the slave robot is configured to drive at least one joint of each of the robotic surgical instruments to follow motion of the handles based on the force control signals and other motion control signals controlling motion of each of the robotic surgical instruments;
   wherein the master console is configured to generate the motion control signals so as to compensate for differences between a position and a velocity of the at least one one joint of each of the handles and a target position and a target velocity for the at least one joint of each of the handles based on target position and velocity values input via the handles, the target position and the target velocity are determined from a position and a velocity of an end effector of each of the robotic surgical instruments, and the position and the velocity of the end effector of each of the robotic surgical instruments are determined from a position and a velocity of the at least one joint of each of the robotic surgical instruments.

8. The surgical robot according to claim 7,
wherein the target position and the target velocity are scaled by a scaling ratio.

9. The surgical robot according to claim 8, wherein the scaling of the target position and the target velocity is performed by one of the master console and the slave robot.

10. The surgical robot according to claim 7, wherein the slave robot is configured to generate the other motion control signals so as to compensate for differences between a position and a velocity of the at least one joint of each of the robotic surgical instruments and a target position and a target velocity for the at least one joint of each of the robotic surgical instruments.

11. The surgical robot according to claim 10, wherein the target position and the target velocity are converted from a position and a velocity of the at least one joint of each of the handles, and are scaled by a scaling ratio.

12. The surgical robot according to claim 11, wherein the scaling of the target position and the target velocity is performed by one of the master console and the slave robot.

13. The surgical robot according to claim 7, wherein the force control signals generated based on the detected forces are scaled by a scaling ratio.

14. The surgical robot according to claim 13, wherein the scaling of the detected forces is performed by one of the master console and the slave robot.

* * * * *